US012186556B2

(12) United States Patent
Shakour et al.

(10) Patent No.: US 12,186,556 B2
(45) Date of Patent: Jan. 7, 2025

(54) NONINVASIVE ELECTRIC BRAIN STIMULATION SYSTEM

(71) Applicant: TECH INNOSPHERE ENGINEERING LTD., Haifa (IL)

(72) Inventors: Ehab Shakour, Haifa (IL); Yousef Badran, Haifa (IL); Gabriel Shakour, Haifa (IL); Rami Shacour, Haifa (IL)

(73) Assignee: TECH INNOSPHERE ENGINEERING LTD., Haifa (IL)

( * ) Notice: Subject to any disclaimer, the term of this patent is extended or adjusted under 35 U.S.C. 154(b) by 0 days.

(21) Appl. No.: 17/735,230

(22) Filed: May 3, 2022

(65) Prior Publication Data
US 2022/0257944 A1    Aug. 18, 2022

Related U.S. Application Data

(63) Continuation of application No. 17/224,160, filed on Apr. 7, 2021, now abandoned, which is a continuation
(Continued)

(51) Int. Cl.
*A61N 1/36* (2006.01)
*A61N 1/04* (2006.01)

(52) U.S. Cl.
CPC ....... *A61N 1/36025* (2013.01); *A61N 1/0456* (2013.01); *A61N 1/0476* (2013.01); *A61N 1/0484* (2013.01); *A61N 1/36034* (2017.08)

(58) Field of Classification Search
None
See application file for complete search history.

(56) References Cited

U.S. PATENT DOCUMENTS

| | | | | |
|---|---|---|---|---|
| 5,885,976 A | * | 3/1999 | Sandyk | A61N 2/002 514/159 |
| 6,488,617 B1 | * | 12/2002 | Katz | A61M 21/00 600/26 |

(Continued)

FOREIGN PATENT DOCUMENTS

| | | |
|---|---|---|
| EP | 2561810 | 2/2013 |
| KR | 101539654 | 7/2015 |
| WO | WO 2015/061004 | 4/2015 |

OTHER PUBLICATIONS

Elmasry, Jessica, Colleen Loo, and Donel Martin. "A systematic review of transcranial electrical stimulation combined with cognitive training." *Restorative neurology and neuroscience* 33.3 (2015): 263-278.
(Continued)

*Primary Examiner* — Carl H Layno
*Assistant Examiner* — Manolis Pahakis
(74) *Attorney, Agent, or Firm* — PEARL COHEN ZEDEK LATZER BARATZ LLP

(57) ABSTRACT

Systems, devices and methods for electric stimulation are provided. The system comprises an electrodes' arrangement configured to be placed in the vicinity of a body region to be stimulated, a signal generator configured to supply electric stimulation signals to the electrodes' arrangement, and a control circuitry connected to the signal generator and to the electrodes' arrangement, the electrodes' arrangement comprises a plurality of electrode elements arranged in a spaced-apart relationship and being connected to the signal generator, so as to define spatial resolution of stimulation, the control circuitry determines data indicative of a profile of a stimulating electric field to be produced by the electrodes' arrangement to stimulate at least one desired target in said body region, and selectively assign, for stimulating each target, at least one pair of first and second effective elec-
(Continued)

trodes, each being formed by one or more of said electrode elements, and enable operation of each of said assigned effective electrodes by the signal generator to produce the stimulating electric field.

1 Claim, 39 Drawing Sheets

Related U.S. Application Data of application No. 15/999,761, filed as application No. PCT/IL2017/050218 on Aug. 24, 2017, now abandoned.

(60) Provisional application No. 62/414,753, filed on Oct. 30, 2016, provisional application No. 62/346,571, filed on Jun. 7, 2016, provisional application No. 62/297,916, filed on Feb. 21, 2016.

(56) References Cited

U.S. PATENT DOCUMENTS

| | | | |
|---|---|---|---|
| 7,047,079 B2 | 5/2006 | Erickson | |
| 8,380,316 B2* | 2/2013 | Hagedorn | A61B 5/375 607/45 |
| 8,845,508 B2* | 9/2014 | Schneider | A61B 5/246 600/14 |
| 8,958,882 B1* | 2/2015 | Hagedorn | A61B 5/6803 607/45 |
| 8,974,365 B2* | 3/2015 | Best | A61K 31/485 600/14 |
| 9,014,811 B2 | 4/2015 | Pal et al. | |
| 9,415,220 B1 | 8/2016 | Spinelli et al. | |
| 2009/0099622 A1* | 4/2009 | Fowler | A61N 1/36082 607/45 |
| 2009/0112278 A1* | 4/2009 | Wingeier | A61B 90/10 607/45 |
| 2009/0149898 A1* | 6/2009 | Hulvershorn | A61N 1/36082 607/45 |
| 2010/0036453 A1* | 2/2010 | Hulvershorn | A61B 5/4064 607/45 |
| 2010/0137938 A1 | 6/2010 | Kishawi et al. | |
| 2010/0204560 A1 | 8/2010 | Salahieh et al. | |
| 2010/0292602 A1* | 11/2010 | Worrell | A61B 5/377 607/45 |
| 2011/0288610 A1* | 11/2011 | Brocke | A61M 21/02 607/45 |
| 2012/0209346 A1* | 8/2012 | Bikson | A61N 1/36034 607/45 |
| 2012/0265261 A1* | 10/2012 | Bikson | A61N 1/0476 607/2 |
| 2012/0330384 A1 | 12/2012 | Perryman et al. | |
| 2013/0079659 A1 | 3/2013 | Akhadov et al. | |
| 2013/0204315 A1* | 8/2013 | Wongsarnpigoon | A61N 1/0484 607/45 |
| 2013/0274593 A1 | 10/2013 | Everling et al. | |
| 2013/0281759 A1 | 10/2013 | Hagedorn et al. | |
| 2014/0057232 A1* | 2/2014 | Wetmore | G09B 19/00 600/28 |
| 2014/0148636 A1* | 5/2014 | Best | A61M 15/00 607/3 |
| 2014/0148872 A1 | 5/2014 | Goldwasser et al. | |
| 2014/0211593 A1* | 7/2014 | Tyler | A61N 7/00 367/137 |
| 2015/0005841 A1* | 1/2015 | Pal | A61N 1/0456 607/45 |
| 2016/0008620 A1* | 1/2016 | Stubbeman | A61B 5/4848 607/45 |
| 2016/0038049 A1* | 2/2016 | Geva | A61N 1/36135 600/300 |
| 2016/0213276 A1* | 7/2016 | Gadot | G16Z 99/00 |
| 2016/0279380 A1* | 9/2016 | Metzger | A61N 1/36025 |
| 2017/0164862 A1* | 6/2017 | Dolev | A61B 5/291 |
| 2017/0197081 A1* | 7/2017 | Charlesworth | A61N 1/36034 |
| 2017/0216595 A1* | 8/2017 | Geva | A61N 1/20 |
| 2017/0296121 A1* | 10/2017 | Dar | A61N 1/0456 |
| 2018/0092565 A1* | 4/2018 | Lee | A61B 5/369 |
| 2018/0311496 A1* | 11/2018 | Lee | A61N 1/0404 |
| 2018/0345006 A1* | 12/2018 | Ambrose | A61B 5/0536 |
| 2019/0001133 A1* | 1/2019 | Onarheim | A61N 1/0456 |
| 2019/0022372 A1* | 1/2019 | Dar | A61N 1/36025 |
| 2019/0082990 A1* | 3/2019 | Poltorak | A61B 5/377 |
| 2019/0083805 A1* | 3/2019 | Etkin | A61B 5/165 |
| 2019/0090749 A1* | 3/2019 | Leuthardt | A61B 5/4064 |
| 2019/0201691 A1* | 7/2019 | Poltorak | A61B 5/0006 |
| 2019/0246927 A1* | 8/2019 | Väyrynen | A61B 5/374 |
| 2019/0247662 A1* | 8/2019 | Poltroak | A61B 5/0816 |
| 2019/0329063 A1* | 10/2019 | Hendler | A61K 31/198 |
| 2019/0336765 A1* | 11/2019 | Charlesworth | A61N 1/0456 |
| 2020/0023189 A1* | 1/2020 | Gribetz | A61N 1/36196 |
| 2020/0164218 A1 | 5/2020 | Glik et al. | |

OTHER PUBLICATIONS

Breitling, C., Zaehle, T., Dannhauer, M., Bonath, B., Tegelbeckers, J., Flechtner, H. H., & Krauel, K. (2016). Improving interference control in ADHD patients with transcranial direct current stimulation (tDCS). *Frontiers in cellular neuroscience*, 10, 72.

* cited by examiner

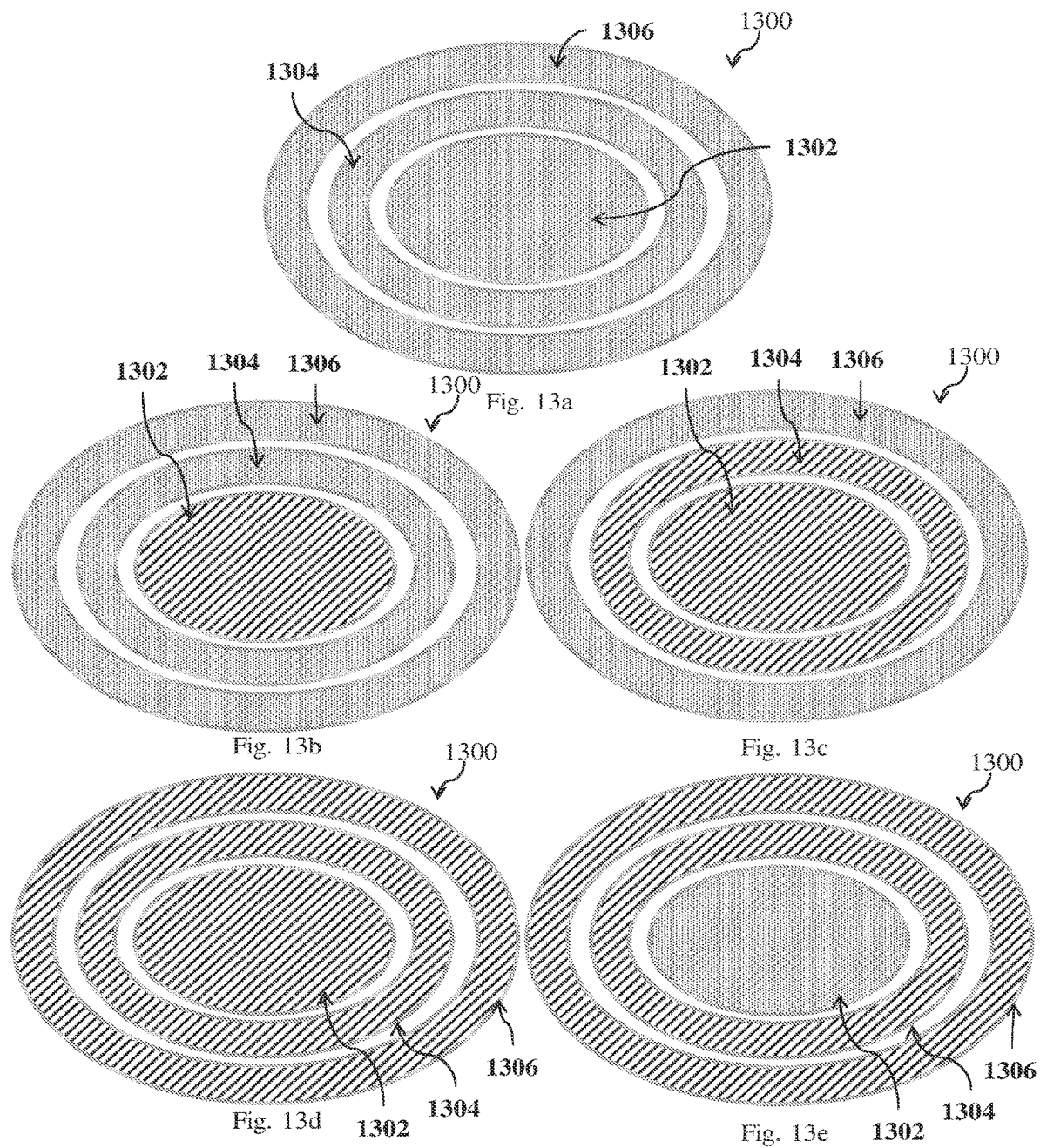

NONINVASIVE ELECTRIC BRAIN STIMULATION SYSTEM

CROSS REFERENCE TO RELATED APPLICATIONS

This application is a continuation of U.S. patent application Ser. No. 17/224,160 filed on Apr. 7, 2021, now abandoned, which is a continuation of U.S. patent application Ser. No. 15/999,761 filed Aug. 20, 2018, now abandoned, which is a US national phase application of PCT International Patent Application No. PCT/IL2017/050218, filed Aug. 24, 2017, which claims the benefit of U.S. Provisional Patent Application No. 62/297,916, filed Feb. 21, 2016, of U.S. Provisional Patent Application No. 62/346,571, filed Jun. 7, 2016, and of U.S. Provisional Patent Application No. 62/414,753, filed Oct. 30, 2016, all of which are incorporated by reference in their entireties.

TECHNOLOGICAL FIELD

The present disclosure is generally in the field of devices for brain stimulation, and relates to a non-invasive brain stimulation system and method, and an electrode arrangement for use in such system.

BACKGROUND

Affecting various brain functions is of great interest to various entities in different industries and under different conditions, ranging from enhancing alertness for pilots, to treating neurodegenerative conditions. Additionally, electric brain stimulation is used for modifying a physiologic or a cognitive condition/property of the subject. Psychiatric/Mental disorders are very common throughout the world, in fact, estimates teach that one out of three people in most countries is reported to suffer from a psychiatric disorder at some point of their lives.

One family of techniques for affecting brain functions is stimulating brain regions by driving electric signal(s) through the crania of the subject. These techniques include transcranial direct current stimulation (tDCS), transcranial alternate current stimulation (tACS) random noise stimulation (RNS) and others. Driving the current signals through the crania is done by placing electrodes on the crania or body of the subject and driving the signal to the subject via the electrodes.

The effect of the stimulation is determined based on the location of the electrodes, their shape and size, as well as the characteristics of the stimulation signal provided to the electrodes. Commonly at least two electrodes are placed on the body, one of the electrodes is placed in close proximity to a body region where the stimulation is intended, and this body region is commonly called target region, and the stimulation signal exits the body back to the stimulation device from the location of the second electrode. The first electrode is commonly called anode or source, while the second electrode is commonly called cathode or drain.

The electrodes that are used repeatedly may have exhaustion caused by previous uses. This might cause a deterioration in their function, such as conductance, or conductance homogeneity.

Commonly, in electric stimulation sessions, the two electrodes might need to be spaced apart in a minimal distance, so that the stimulation signal does not pass directly from one electrode to the other neighboring one without affecting the body region. This minimal distance constraint limits the ability to stimulate adjacent target regions.

Currently, the most effective treatment for most psychiatric/mental disorders includes consumption of pharmaceutical drugs that are categorized as psychiatric medications, and are comprised of several main groups such as antidepressants, anxiolytics, mood stabilizers, antipsychotics, and stimulants. Many of the used drugs have very limited efficacy, and many are associated with undesired side effects. Additionally, many of the used drugs affect the symptoms only temporarily for a limited amount of time, as low as a few hours, however they do not solve the disorder itself.

GENERAL DESCRIPTION

As indicated above, brain functions can be affected by stimulating brain regions by driving electric signal(s) through the crania of the subject. However, for targeting specific brain regions associated with a desired cognitive function/activity, the electrodes need to be placed at certain locations/positions on the crania and/or body of the subject. Commonly, the placement of the electrodes is done by neuro science professionals using aiding mechanisms such as EEG 10/20 head caps for estimating the place of the electrodes for affecting a desired brain region. This process is complicated and requires a high level of expertise, and relies on the proficiency and accuracy of the expert, and misplacement of the electrodes can impair the effectiveness of the stimulation.

There is thus a need in the art for novel noninvasive electric brain stimulation techniques utilizing electrodes positioning mechanisms for facilitating easy and accurate electrode placement for effective brain stimulation.

In various stimulation techniques, such as transcranial current stimulation or transcranial direct current stimulation, while stimulation may occur in regions in the vicinity of the anode(s), the regions near the cathode(s) are generally inhibited. This is an undesired effect of the stimulation; therefore, the cathodes are commonly placed near regions where inhibition may not be of severe consequences. Especially in brain stimulation, stimulating one brain region, while not suffering an unintended inhibition of a different region, is desired. Additionally, when electrodes are placed on the scalp of the user/subject to target an underlying brain region, there is generally a degree of uncertainty as to the exact location of the underlying target brain region. Thus, the stimulation does not always reach or cover the target region(s).

There is therefore a need in the art for mitigating the risk of misplacement of electrodes and/or mitigating the undesired inhibition effect of cathodes, or undesired stimulation/excitation effect of anodes if cathodal inhibition is desired.

Also, there is a need for a novel non-invasive electric stimulation technique enabling treatment of psychiatric/mental disorders, providing treatment alternatives to drugs, having lower side effects and providing treatment to the disorder, not only by masking of the symptoms.

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to the invention, there are provided herein devices, systems and methods for providing electric brain stimulation to desired brain region(s) by emulating the effect of positioning electrodes at specific location on the subject. According to some embodiments, the emulation of the effect of positioning electrodes at specific locations on the subjects is done by providing a plurality of electrodes to the subject and selecting electrodes according to the desired emulated electrode locations that are associated with affecting stimulation to the desired brain region.

According to the invention, there are provided herein devices, systems and methods for providing electric brain stimulation to more than one brain region by selecting electrodes to emulate an electrode placement associated with affecting stimulation to one desired brain region, then or simultaneously selecting electrodes to emulate an electrode placement associated with affecting stimulation to another brain region.

According to the invention, there are provided devices, systems and methods for delivering electric stimulation, wherein the location(s) through-which the signal is provided to the body may change during the stimulation of a certain brain region(s).

It has been found that the inhibition effect of cathodal stimulation may be mitigated or cancelled if the stimulation does not last for more than a certain amount of time, such as two minutes or other times based on the location of the electrodes and characteristics of the stimulation signal.

According to the invention, a plurality of electrodes are provided, and of which, a first set of at least one electrode is selected to form a first cluster of electrodes, and a second set of electrodes is selected to form a second cluster of electrodes, then, a stimulation signal is delivered through the first cluster of electrodes and the second cluster of electrodes for a certain amount of time, then the electrode selection of the first set (and/or the second set) is/are changed to form a different area of contact with the stimulated body, while the stimulation signal is delivered.

The electrode selection of the first and/or second electrode sets are changed for driving the stimulation signal to/from a different location on the body of the user at/before a certain time period, thereby limiting the inhibition time of a region, and mitigating or removing the inhibition effect thereto. The change in electrode selection for the first set (and/or second set) may be such that at least a certain sub-region, being main region, remains selected, and a surrounding/peripheral region selection is changed, thereby a stimulation to a region of higher location certainty is maintained, while stimulation to regions with lesser certainty can be altered, the selection change is determined based on the region location certainty, such that regions with higher certainty may get selected more often (or always), and other regions with less certainty get selected less often for stimulation.

According to the invention, there are provided herein devices, systems and methods for electric stimulation, such as brain stimulation, in which the stimulation signal is provided from different locations during the stimulation, to thereby mitigate the effect of stimulating an undesired region due to electrode misplacement, mitigate undesired effects of cathodal inhibition when anodal stimulation/excitation is desired, mitigate undesired effects of anodal excitation when cathodal inhibition is desired, and/or adjust the path/target of the stimulation signal during stimulation.

As indicated above, the invention also provides for non-invasive treatment of mental disorders, which may be used as alternatives to drugs, having lower side effects and provide treatment to the disorder, not only by masking of the symptoms.

According to the invention, there are provided herein methods, systems and devices for non-invasive electric brain stimulation for stimulating target brain regions associated with the mental disorder, thereby stimulating the neural activity of some brain regions and/or inhibiting the neural activity of some brain regions. According to some embodiments, the brain regions that the neural activity thereof is stimulated, are associated with lower than normal neural activity in people suffering from the disorder, and the brain regions that the neural activity thereof is inhibited, are associated with a higher than normal neural activity in people suffering from the disorder.

Inducing nonelectric brain stimulation for stimulating the neural activity of certain brain regions may be done by applying a stimulation signal configured to increase the neural plasticity at the desired brain region, thereby increasing or stimulating the structuring of new neural structures, to thereby enhance the activity of the stimulated brain region, and moving it towards the normal neural activity.

Inducing nonelectric brain stimulation for inhibiting the neural activity of certain brain regions may be done by applying a stimulation signal configured to decrease the neural plasticity at the desired brain region, thereby reducing or inhibiting the structuring of new neural structures, to thereby decrease or eliminate the activity of the stimulated brain region, and moving it towards the normal neural activity.

According to the invention, electric stimulation signal may be noninvasively provided for affecting stimulation/inhibition of more than one brain region during a treatment session. A plurality of treatment sessions may be provided, each of the sessions being configured to apply stimulation to one or more of the target brain regions.

According to the invention, the devices and/or systems may be configured to provide treatment sessions based on a prescription/diagnosis of a mental disorder or a symptom thereof. The number of stimulation sessions configured to be provided by the device may be based on the prescription/diagnosis of a mental disorder or a symptom thereof. The stimulation characteristics, for the stimulation signal provided to at least one of the target brain regions, may be selected based on the prescription/diagnosis of a mental disorder or a symptom thereof. According to the invention, the device may be configured to have a minimal break time between treatment sessions, e.g. based on the prescription/diagnosis of the mental disorder. The device may also be configured to provide a limited number of stimulation sessions per period of time, based on a prescription/diagnosis of the mental disorder.

The mental/psychiatric disorders may include Attention deficit disorders, such as ADD and/or ADHD, clinical depression, insomnia, bipolar disorder, schizophrenia and others.

The target brain regions may be brain regions in the frontal lobe, temporal lobe, parietal lobe, occipital lobe and/or the cerebellum.

Thus, according to a first broad aspect of the invention, there is provided an electric stimulation system, comprising: an electrodes' arrangement configured to be placed in the vicinity of a body region to be stimulated; a signal generator configured to supply electric stimulation signals to the electrodes' arrangement; and a control circuitry connected to the signal generator and to the electrodes' arrangement, wherein the electrodes' arrangement is configured for covering the body region and comprises a plurality of electrode elements arranged in a spaced-apart relationship and being connected to the signal generator, so as to define spatial resolution of stimulation; and the control circuitry is configured and operable to determine data indicative of a profile of a stimulating electric field to be produced by the electrodes' arrangement to stimulate at least one desired target in said body region, and selectively assign, for stimulating each target, at least one pair of first and second effective electrodes, each effective electrode being formed by one or more of said electrode elements of the electrodes' arrangement, and enable operation of each of said assigned effective electrodes by the signal generator to produce the stimulating electric field in accordance with said profile.

The stimulating electric field profile is characterized by two or more of the following parameters: electric field region location and shape with respect to a location of said at least one desired target within said body region, field intensity profile, field frequency profile, electric field duration, a time pattern of the electric field.

In some embodiments, the control circuitry comprises a controller configured to analyze data indicative of the at least one desired target within the body region and determine a number n (n≥1) and location of electrode elements in said electrodes' arrangement to define each of said pairs of first and second effective electrodes to be assigned in accordance with said desired target. The data indicative of the at least one desired target may comprise target location data within said body region and/or geometrical data about said target.

The data indicative of the at least one desired target may comprise at least one of the following: stimulation field intensity, stimulation field frequency profile, stimulation field duration, and a time pattern of application of the stimulation field.

In some embodiments, the control circuitry comprises a switching arrangement comprising a plurality of switches associated with a plurality of electrode elements of the electrodes' arrangement to selectively switch each of the electrode elements between its operative and inoperative states in accordance with the assignment of said at least first and second effective electrodes.

In some embodiments, the control circuitry is configured and operable to operate at least two successive treatment sessions to said at least one desired target within the body region by assigning a first effective electrode as an anode to be activated in the at least two successive treatment sessions, and at least two effective electrodes as cathodes, each to be activated with the anode in each treatment session, thereby stimulating the at least one desired target while mitigating inhibiting other regions in the body region.

In some embodiments, each of the electrode elements is assigned with its unique identification data, said control circuitry utilizes the identification data of the electrode elements to assign said selected at least first and second effective electrodes.

In some embodiments, the electrodes' arrangement comprises an insulator layer located adjacent to at least some of said electrode elements, thereby enabling to reduce the space between said at least some of electrode elements and increase the spatial resolution of stimulation.

In some embodiments, the electrodes' arrangement is arranged on a cap or hat-like structure configured to be positioned on a subject's scalp.

According to another broad aspect of the invention, there is provided an electrodes' arrangement for use in an electric stimulation system, the electrodes' arrangement being configured to be placed in the vicinity of a body region to be stimulated, and comprises a plurality of electrode elements arranged in a spaced-apart relationship so as to define spatial resolution of stimulation; said electrode elements being configured to be operated in groups of one or more electrode elements to thereby define at least one pair of first and second effective electrodes to produce a stimulating electric field of a predetermined profile in at least one desired target in said body region.

According to yet another broad aspect of the invention, there is provided a method for electrically stimulating a desired target in a body region, the method comprising:

placing an electrodes' arrangement in the vicinity of the body region, such that the electrodes' arrangement covers the body region by a plurality of electrode elements arranged in a spaced-apart relationship, so as to define spatial resolution of stimulation;

receiving data indicative of at least one desired target in said body region;

analyzing said data indicative of the at least one desired target, and determining data indicative of a profile of a stimulating electric field to be produced by the electrodes' arrangement to stimulate said at least one desired target, analyzing said data indicative of the profile of the stimulating electric field, and assigning at least first and second effective electrodes, each formed by one or more of the electrode elements of the electrodes' arrangement, to be operated to produce the stimulating electric field in accordance with said profile; and supplying electric stimulation signals to the effective electrodes.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings.

In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below, in which:

FIGS. 13a-e schematically illustrate electrode set selection of an array of electrode, according to some embodiments;

DETAILED DESCRIPTION OF EMBODIMENTS

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The invention, in some of its aspects, provides a device for emulating electrode positioning to affect a stimulation to a desired body (e.g. brain) region(s) by providing a plurality of electrodes configured to be placed on the subject's body, and a selector/switching unit configured to connect one or more of the electrodes (appropriately selected) to an electric signal driver, thereby emulating the effect of having an electrode positioned at a desired position and connected to the electric signal driver.

Figure 1A:
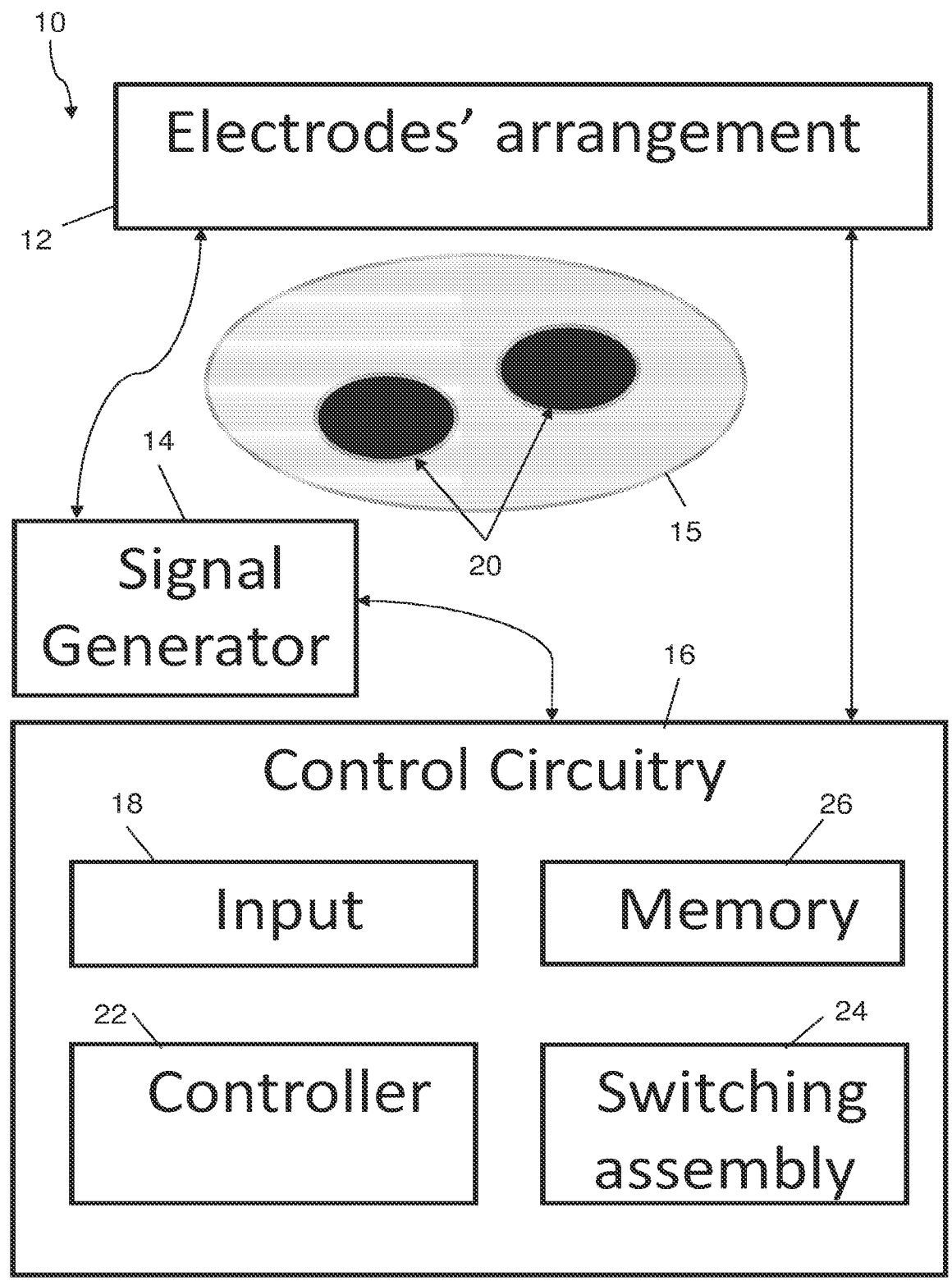
FIG. 1a is a block diagram of an electric stimulation system according to the invention.

Referring to FIG. 1a, there is illustrated, by way of a block diagram, main functional parts of an electric stimulation system 10 according to the invention. The system 10 includes an electrodes' arrangement 12 which is configured to be placed in the vicinity of a body region 15 to be stimulated; a signal generator 14 configured to supply electric stimulation signals to the electrodes' arrangement; and a control circuitry 16 connected to the signal generator 14 and to the electrodes' arrangement 12. The control circuitry 16 is configured and operable to determine data indicative of a profile of a stimulating electric field to be applied by the electrodes' arrangement to the body region to affect/stimulate at least one desired target 20 in the body region. The control circuitry may include an input utility 18 configured and operable to receive input data, and may also include a memory 26 in which the data is saved to be available for access, analyze the data and determine the data indicative of the profile of a stimulating electric field to be applied. The control circuitry 16 then operates to assign at least first and second effective electrodes from the electrodes' arrangement 12 to be operated by the signal generator 14 to produce the stimulating electric field in accordance with the so-determined stimulating electric field profile.

It should be understood that stimulation electric field is created via electric supply to the effective electrodes (potential difference created via current or voltage input to the electrodes). The stimulation driven signal is a current signal (ionic current), directly tight to the electric field, and the electric field may change according to the media (head of the user) and it varies between participants. In the description below such stimulation signal/effect is referred to as electric field.

As will be described more specifically further below, the stimulating electric field profile is characterized by two or more of the following parameters; electric field region location and shape with respect to a location of the desired stimulation target within the body region, field intensity profile, field frequency profile, electric field duration, a time pattern of the electric field application (e.g. sequence of pulses). To this end, the control circuitry analyzes input data including data indicative of the location and possibly also shape/geometry of the desired stimulation target within the body region, and utilizes previously provided (and possibly stored in memory) data about the electrodes' arrangement, namely number of electrode elements/sub-electrodes, distances between the electrode elements, electric connections between the electrode elements, etc.

The control circuitry 16 includes a controller 22 which is configured to utilize the data indicative of the desired stimulation target and the data about the electrodes' arrangement, and determines/selects a number n (n≥1) and location of electrode elements in the electrodes' arrangement to define each of the first and second effective electrodes to be assigned in accordance with the desired stimulation target and desired stimulation effect (caused by the stimulation field profile). Such pair of first and second effective electrodes is then operated as an anode-cathode pair to create the desired electric field profile in the desired stimulation target. To this end, the control circuitry includes a switching arrangement 24 which includes a plurality of switches associated with a plurality of electrode elements of the electrode arrangement to selectively switch each of the electrode elements between its operative and inoperative states in accordance with the assignment of the effective electrodes.

Figure 1B:
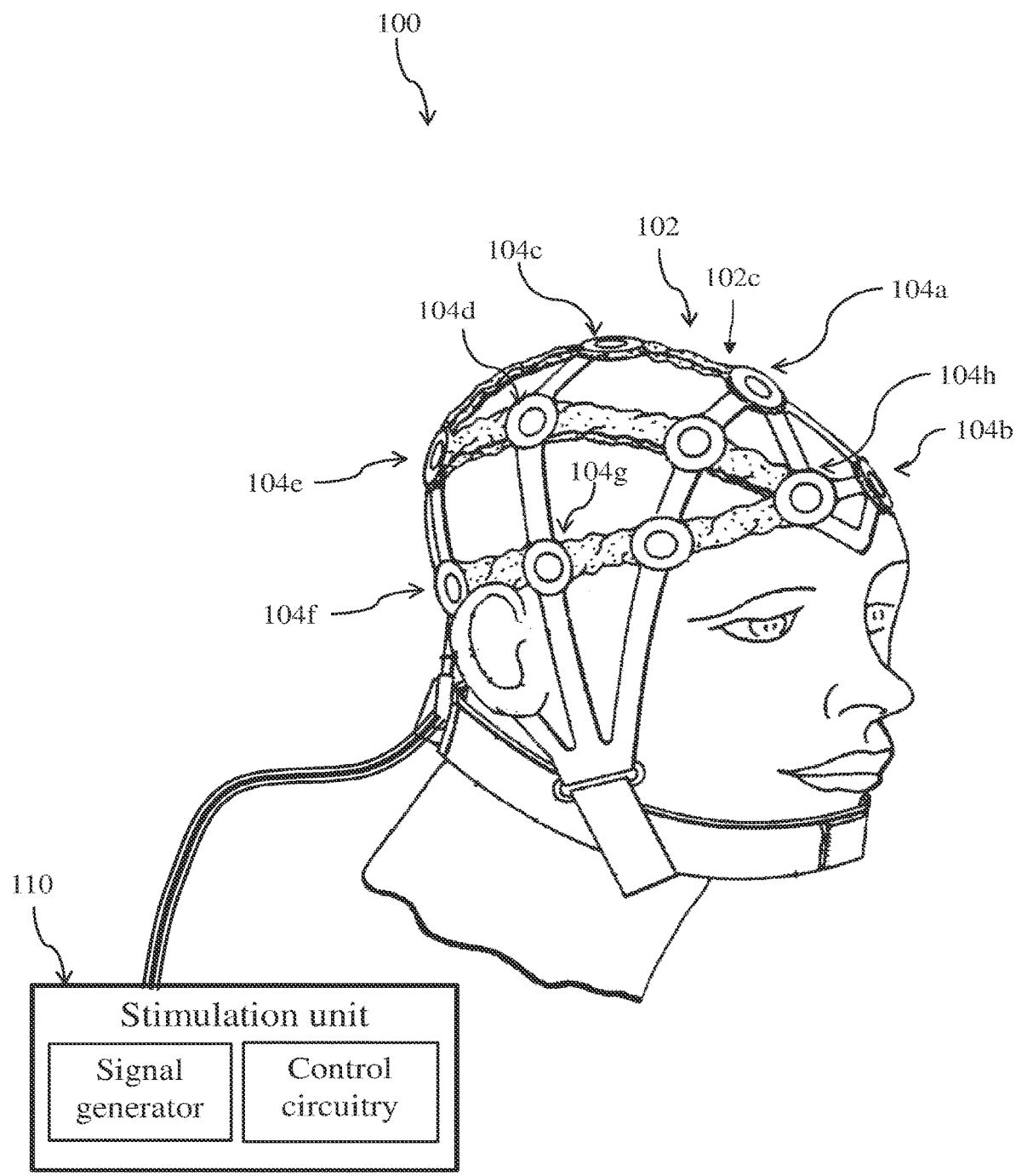
FIG. 1b schematically illustrates the stimulation system of the invention being applied for stimulation of desired target region(s) in patient's brain.

Reference is made to FIG. 1b, which schematically illustrates a system for brain stimulation using an arrangement of electrodes. The system is configured and operable for emulating desired electrode positioning on a subject's head for applying electric stimulation to a predetermined brain region. In the example shown, a system 100 includes an electrodes' arrangement configured as electrode array 102, which includes a plurality of electrodes/electrode elements/sub-electrodes, such as electrodes 104a-104h and is configured to be placed on a subject such as the subject's head, and a stimulation unit 110 (formed by signal generator 12 and control circuitry 16 of FIG. 1a) configured to selectively provide electric signal(s) to at least some of the plurality of electrodes in the electrode array 102. The electrode array can be organized on a suitable structure that conforms to the body organ to ensure good contact therebetween. As shown in the figure, the electrode array 102 is placed on a cap 102c conforming to the subject's head.

As described above, the stimulation unit 110 operates to select at least first and second effective electrodes. The selection of the effective electrodes' pair is based at least on such factors as the required sizes of the effective electrodes, distance between them and each of them from the desired target location. According to some embodiments, the stimulation unit 110 is configured to select a first set of electrodes/ electrode elements (the set includes one or more of the electrode elements) to be connected to a first electric signal port (not shown), and to select second set of electrodes (including one or more electrodes) to be connected to a second electric signal port (not shown). For example, electrodes 104e, 104f and 104g are selected to be a first set to emulate a first effective electrode positioned at one position, and electrodes 104a and 104b are selected to be a second set to emulate a second effective electrode positioned at another position. The first set may emulate a cathode while the second set may emulate an anode, or vise versa.

Generally, emulating an effective electrode includes emulating one or more of the following: position of the effective electrode, shape of the effective electrode, surface area of the effective electrode, and more. It should be understood that the desired parameters of the effective electrode may be achieved by forming the effective electrode from two or more electrically connected electrode elements.

According to some embodiments, in one iteration, the first and second sets of electrodes are selected for emulating positions and characteristics of respective first and second electrodes (e.g. first cathode-anode pair) for stimulating a first brain region (constituting first desired target), and then third and fourth sets are selected to emulate positions and characteristics of third and fourth electrodes (second cathode-anode pair) for stimulating a second brain region (constituting second desired target). It should be understood that the electrodes' pair is defined by electric field profile to be provided/created in a desired region. In other words, the electric field profile is characterized by such factors as location within the body, field intensity, polarity, as well as time pattern (i.e. duration and time variation).

Figure 2A:
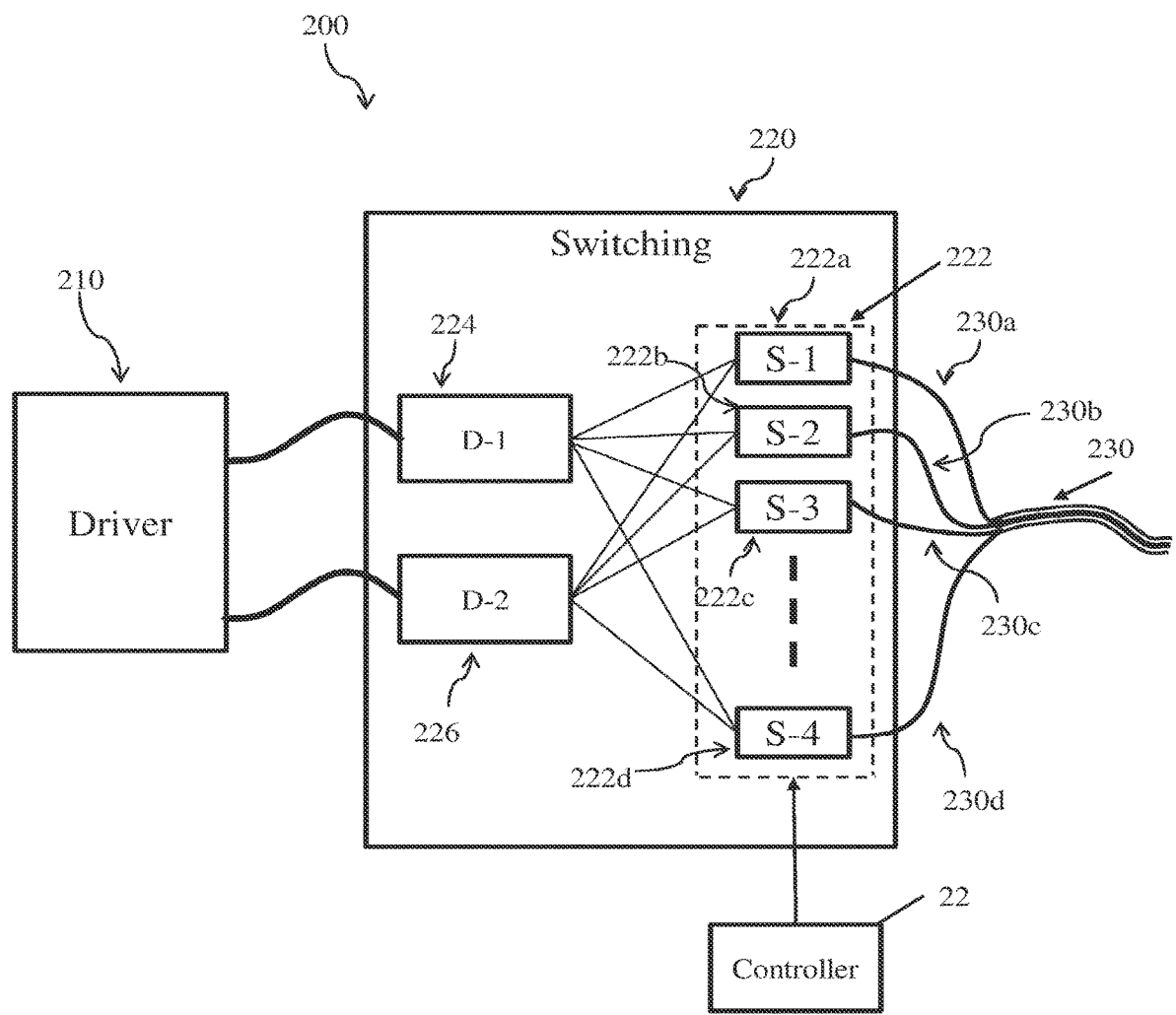
FIG. 2a schematically illustrates a switching mechanism and stimulation driver, according to some embodiments.

Reference is now made to FIG. 2a, which illustrates a specific but not limiting example of the configuration and operation of a switching mechanism 200. The switching mechanism is implemented by a switching assembly/circuitry 220 (24 in FIG. 1A) which is connected to the signal generator/driver 210, and is also connected to the electrodes' arrangement (not shown here) via connection assembly 230.

As exemplified in the figure, the switching assembly 220 includes a switches' arrangement 222 formed by a plurality of switches 222a-222d which are configured to be connected to a plurality of associated electrodes via links 230a-230d respectively. Each of the switches 222a-222d is controllably shifted (by the controller 22 of the control circuitry) between its operative positions and an inoperative position, such that the switch in its operative positions connects the associated electrode element to a first port 224 or a second port 226 of the signal generator/driver, and in the inoperative position disconnects the electrode from any of the driver ports. Ports 224 and 226 are configured to be connected to driver/signal generator 210 for obtaining (while being controlled by the control circuitry) an electric signal for stimulation.

According to some embodiments, the stimulation driver 210 may be a pre-configured or configurable electric stimulation driver. The electric signal provided by the stimulation driver may include a current signal (DC or AC current, which may include noise, pulses or other forms of signals), or an electric potential signal.

Figure 2B:
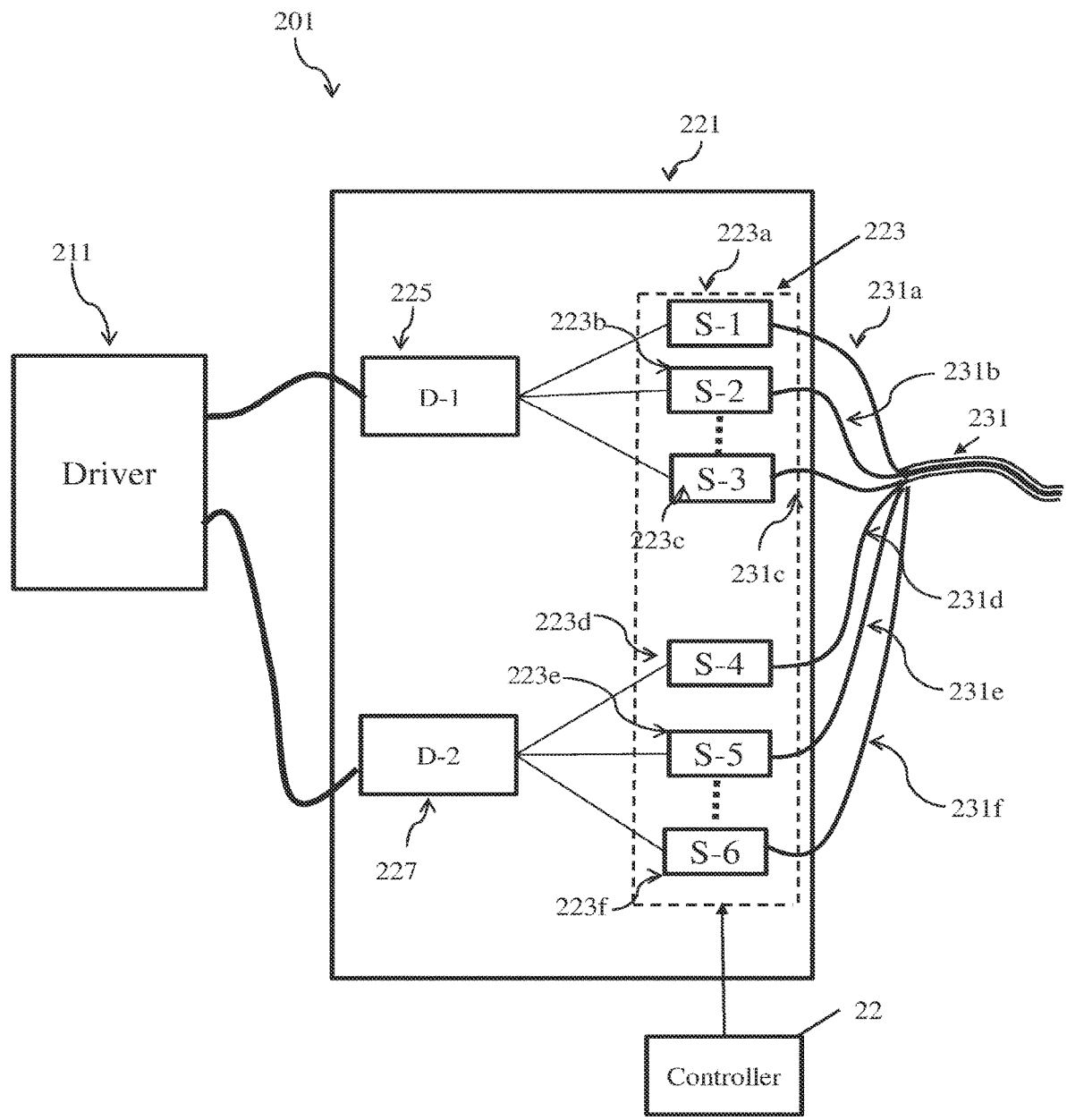
FIG. 2b schematically illustrates a switching mechanism and stimulation driver, according to some embodiments.

Reference is made to FIG. 2b, which illustrates another specific but not limiting example of the configuration and operation of a switching mechanism 201 implemented by a switching assembly 221 and connected to a stimulation driver 211, the controller 22 and electrode's arrangement via connection assembly 231. As exemplified, the switching assembly 221 includes a switches' arrangement 223 formed by a plurality of a first set of switches 223a-223c configured to be connected to a first set of electrodes via connection links 231a-231c respectively to controllably connect/disconnect the associated electrodes with port 225 to emulate a first effective electrode position and characteristics, while a second set of switches 223d-223f is configured to be connected to a second set of electrodes via links 231d-231f respectively to controllably connect/disconnect the associated electrodes with port 227 to emulate a second effective electrode position and characteristics. As shown, ports 225 and 227 are configured to be connected to the signal generator/driver 211 for obtaining an electric signal for stimulation, while being controlled by the controller 22.

It should be noted that one of the main differences between the configurations shown in FIGS. 2a and 2b, is that in FIG. 2a each electrode element can function as an anode or as a cathode, because every electrode element is connected to both ports 224 and 226. However, in the configuration of FIG. 2b, each electrode element is connected to one of the ports 225 and 227, and therefore the first set of electrodes can function as anode and the second set as cathode, or vice versa (if the polarity is changed at the driver 211), at each single activation act/session.

Figure 3:
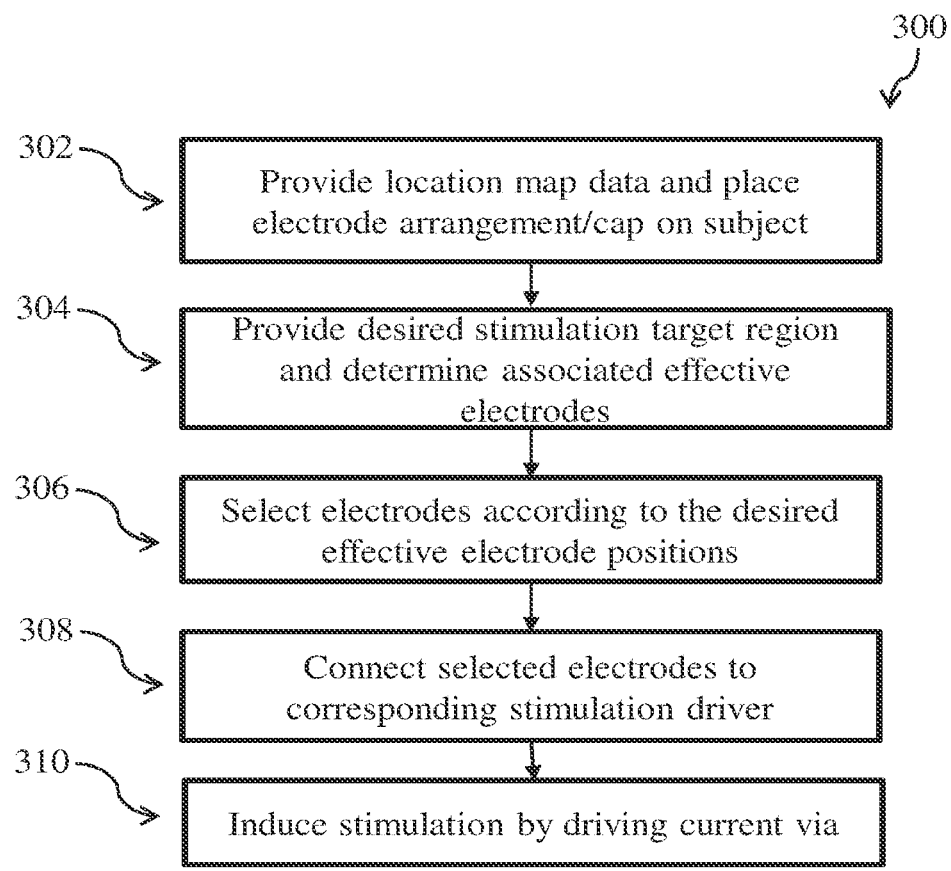
FIG. 3 schematically illustrates a method for emulating electrode positioning, according to some embodiments.

Reference is now made to FIG. 3, which schematically illustrates an example of a flow diagram 300 of a method for emulating electrode positioning for defining the first and second effective electrodes to be used in a certain stimulation session. Initially, an electrodes' arrangement (including a plurality of electrode elements, e.g. electrodes arranged on a cap) is placed on a subject and data indicative of the arrangement of electrode elements with respect to the brain region, i.e. location map data, is provided (e.g. is stored in the memory)—(step 302). The mapping of the electrodes' locations will be exemplified further below. Independently, data/information related to a desired stimulation target in the brain region is provided or accessed from a memory (e.g. being previously determined from EEG or MRI measurements, as the case may be). The target related data and the location map data are analyzed to determine associated effective electrode positions and characteristics (step 304). Then, at least a first set of electrodes and a second set of electrodes are selected according to the desired effective electrode positions and characteristics (step 306), then the at least first set and second set of selected electrode are shifted into their operative positions by the switching assembly to be connected to the signal generator. e.g. respective stimulation drivers or ports (step 308), and an electric stimulation is induced (stimulation session is initiated) by providing an electric signal through the at least first set and second set of electrodes (step 310), thereby applying the stimulation electric field of the desired profile to the desired target.

As described above, the set of electrodes selected to emulate a position and characteristics of a stimulation effective electrode may include one or more electrodes. According to some embodiments, the stimulation driver (signal generator) is a current stimulation driver such as tDCS, tACS, RNS, tPCS or the like.

Figure 4:
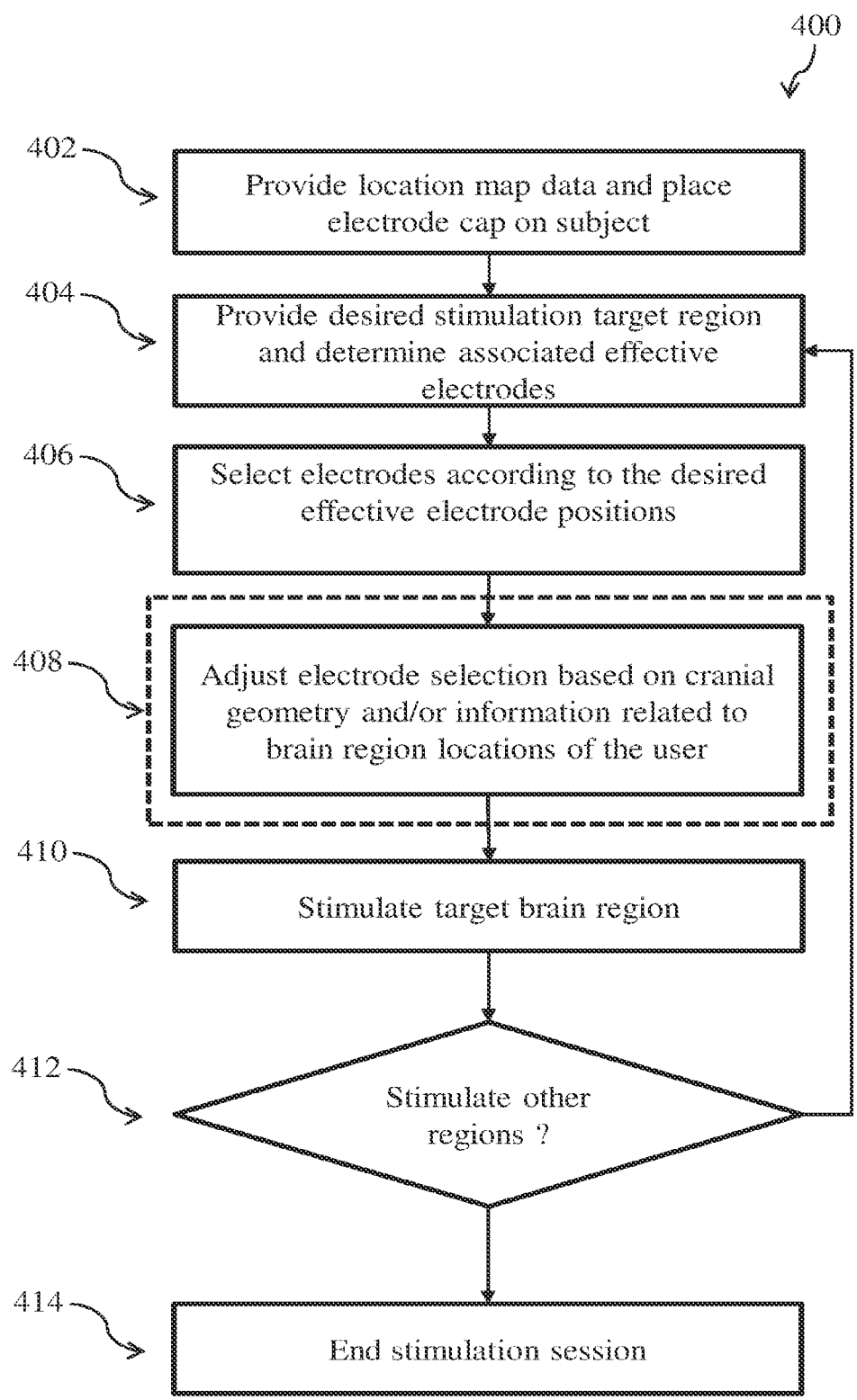
FIG. 4 schematically illustrates a method for emulating electrode positioning for inducing stimulation to more than one brain region, according to some embodiments.

Reference is now made to FIG. 4, which schematically illustrates an example of a flow diagram 400 of a method for emulating electrode positioning for inducing stimulation to more than one desired targets in the brain region. Similarly to the above described example of FIG. 3, initially an electrodes' arrangement/cap having a plurality of electrodes is placed on a subject and data about such arrangement is provided (step 402), and data/information related to a desired stimulation target in the brain region is independently provided and used to determine the associated effective electrodes (step 404). Then, two or more electrode sets are selected based on the position/place of the target brain region(s) (step 406), and optionally the electrode selection may be further adjusted based on the geometry of the crania of the specific subject, or based on previous learnings, or by searching for more efficient stimulation locations of emulated effective electrodes (step 408). Then, a stimulating session is initiated/operated for stimulating the target brain region(s) by driving a stimulating electric signal through the two or more sets of electrodes (step 410). If other stimulations are needed (step 412), another (or the same) target brain region is obtained and the process is repeated from step 404, and if not, the stimulation session is terminated (step 414).

In the following, various embodiments of electrode emulation devices according to the invention, utilizing electrode arrangement/array, are described.

Figure 5A:
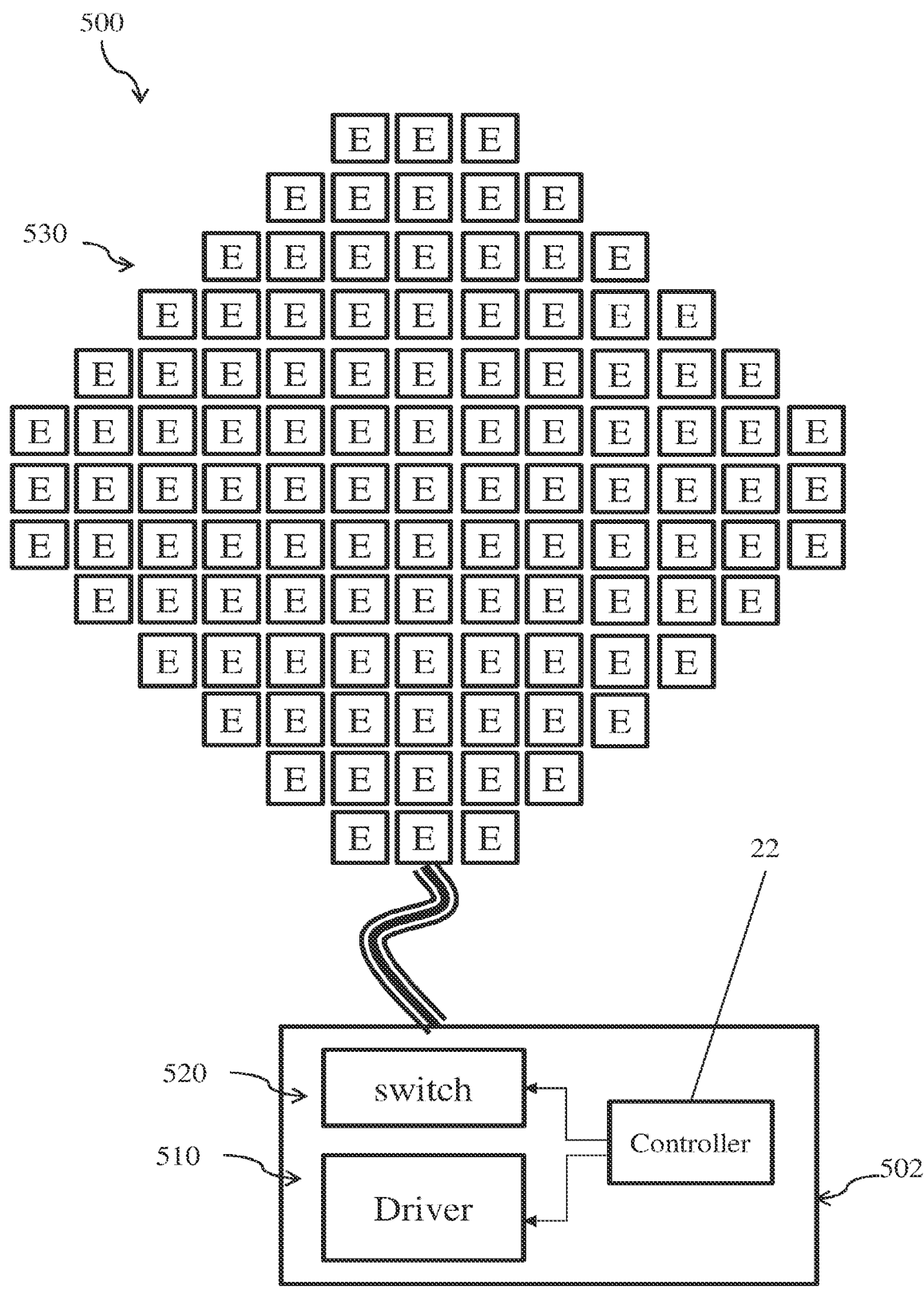
FIG. 5a schematically illustrates an electrode emulation device, according to some embodiments.

Reference is made to FIG. 5a, which schematically illustrates an electrode emulation device 500 which includes a main stimulation unit 502 (similar to stimulation unit 110) having a signal generator/driver 510 configured to drive an electric stimulation signal, a switching assembly 520 which includes a switch's arrangement for selecting which electrodes or electrode elements of the electrode arrangement/array 530 may be connected to receive the electric stimulation signal from the signal generator/driver 510, and a control circuitry/controller 22 connected to the signal generator and the switching assembly for controlling both in accordance with the described above after receiving data indicative of the desired stimulation target. The selection of specific electrodes from the electrode array 530 is generated by the controller 22 and may emulate a placement of effective electrodes of different sizes and shapes on the crania of a subject to match the desired electric field generated at the desired target region, as will be further described below.

Generally, the electrode arrangement 530 may include a variety of electrode numbers, with the electrodes being either similar or different with respect to their size (surface area), shape or distance therebetween. This provides the user with a wide choice of possible combinations to enable generation of the desired parameters (e.g. location, intensity, time pattern) of the electric field inside the body. In the non-limiting example shown, the electrodes have similar size and shape.

According to some embodiments, the electrode array 530 may include 10-20, 20-40, 40-60, 60-80, 80-100, or more than 100 electrodes. In some embodiments, at least some of the electrodes in the electrode array are rectangular electrodes. In some embodiments, at least some of the electrodes in the electrode array are triangular electrodes. In some embodiments, at least some of the electrodes in the electrode array are circular and/or oval electrodes. In some embodiments, at least some of the electrodes in the electrode array are electrodes having a polygonal shape. In some embodiments, the spacing between the electrodes is approximately 2 mm. In some embodiments, the spacing between the electrodes is less than 3 cm. In some embodiments, the spacing between the electrodes is in the range of 0.5 mm to 1 cm.

According to some embodiments, the electrode array includes more electrodes, and the achieved emulation resolution may be greater. In such case, the electrodes can be configured to be smaller so that the overall surface area on the electrode cap, or whatever suitable housing, stays the same.

Figure 5B:
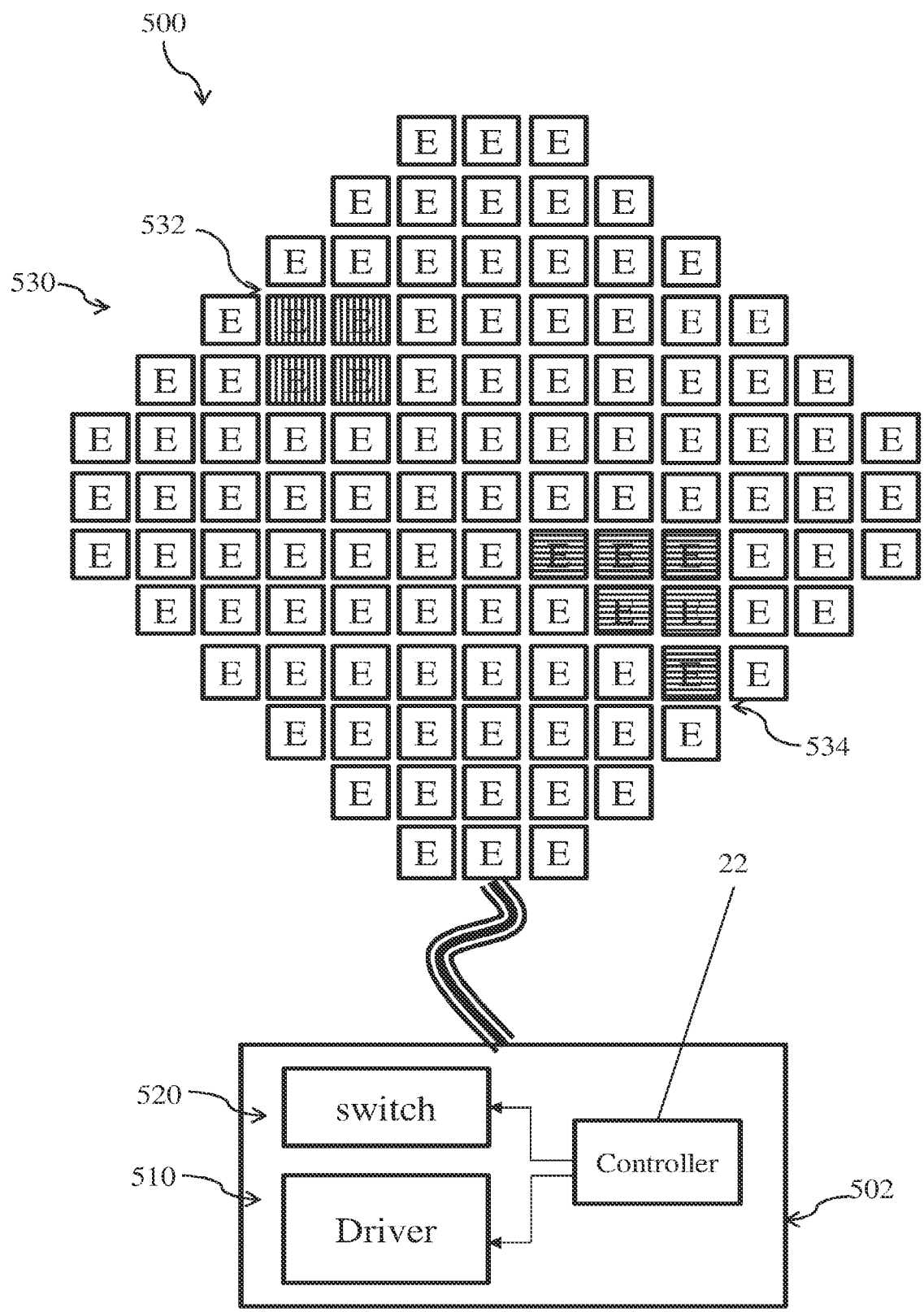
FIG. 5b schematically illustrates an electrode emulation device with preliminary electrode emulation, according to some embodiments.
Figure 5C:
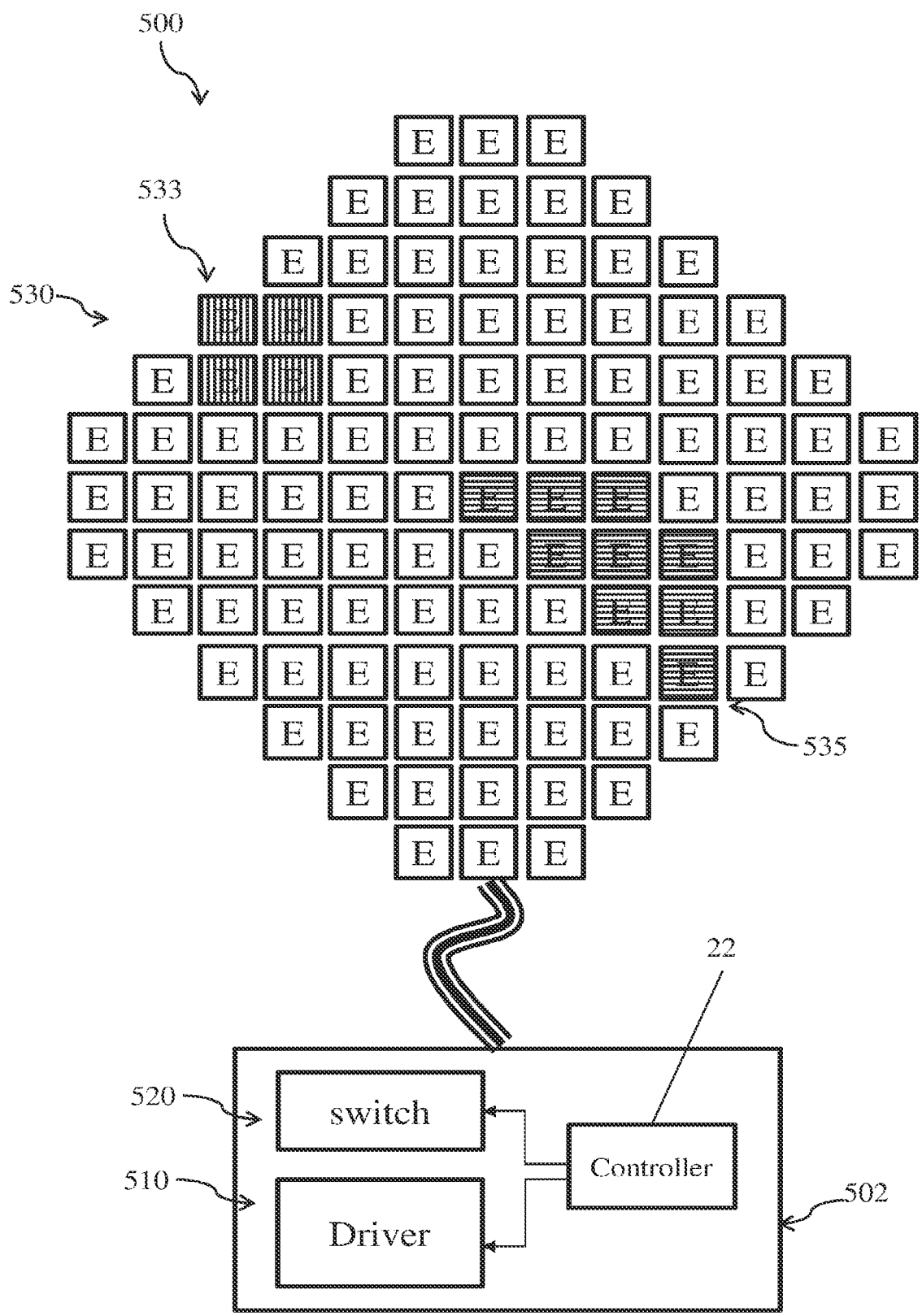
FIG. 5c schematically illustrates an electrode emulation device with adjusted electrode emulation, according to some embodiments.

Reference is now made to FIG. 5b, which schematically illustrates one embodiment of the electrode emulation device with emulation of two effective electrodes by selecting/combining a plurality of electrode elements in the electrode arrangement, to provide a pair of anode-cathode effective electrodes. The control circuitry/controller 22 chooses electrodes from the electrode array in accordance with data received being indicative of the stimulation target inside the body. As shown, a first set of electrodes 532 is selected, to emulate a first effective electrode position and shape, and a second set of electrodes 534 is selected to emulate a second effective electrode position and shape. The two effective electrodes function as anode and cathode to create the desired electric field responsible for stimulating the desired stimulation target. FIG. 5c illustrates how the electrode emulation device, i.e. its controller, can adjust the emulation of the effective electrodes. The electrode selection is adjusted based on user-specific parameters, and an adjusted first set of effective electrodes 533 is selected to emulate a first effective electrode with adjusted position and shape, and an adjusted second set of electrodes 535 is selected to emulate a second effective electrode with adjusted position and shape, to thereby alter the parameters of the generated electric field inside the body. The adjustment may be based on the size of the crania of the subject, or on previous learning and efficacy assessment of the stimulation for the subject. In some embodiments, the adjustment may be done for assessing the efficacy of a changed position and/or shape of an electrode.

Figure 6:
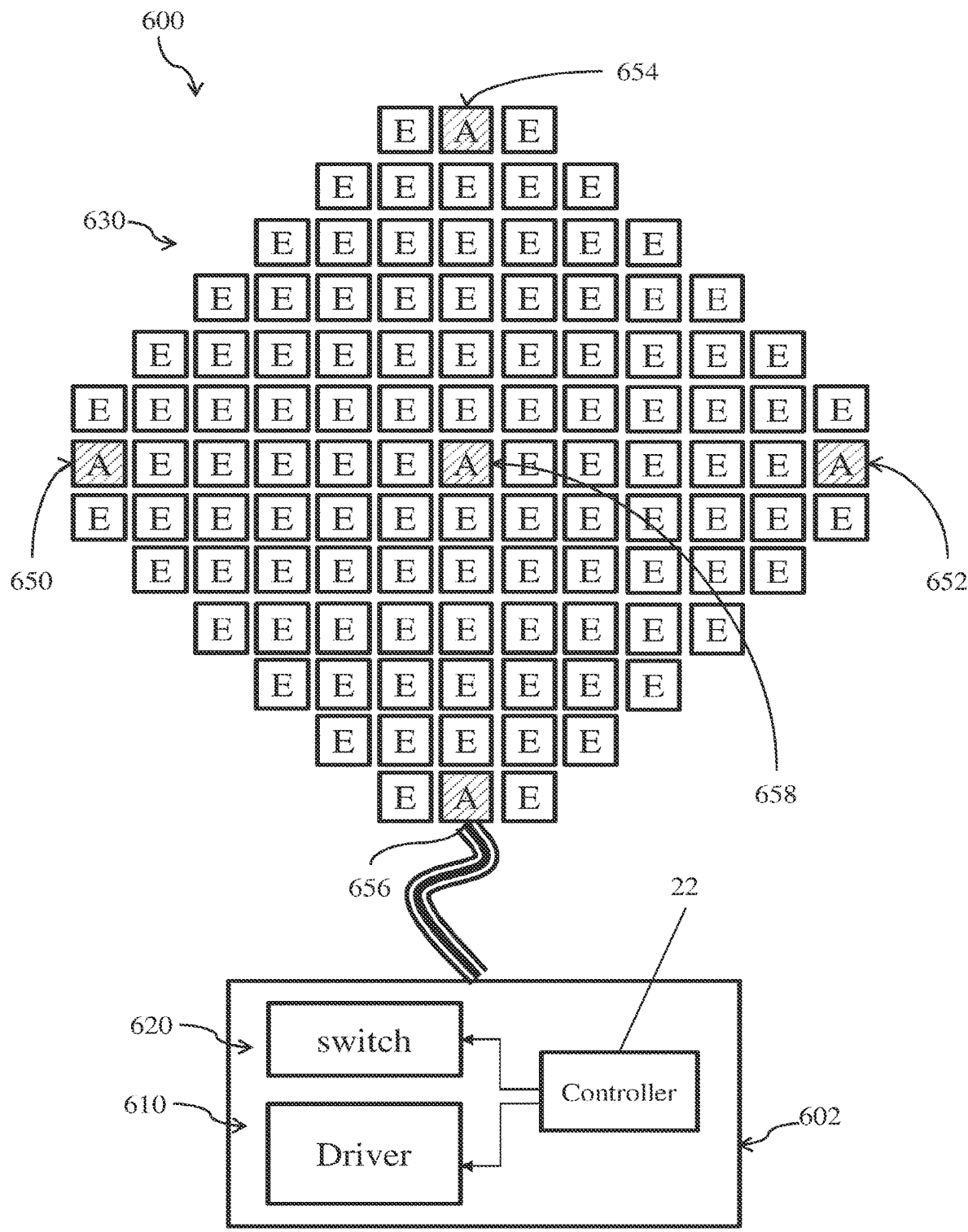
FIG. 6 schematically illustrates an electrode emulation device with reference points, according to some embodiments.

Reference is made to FIG. 6, which schematically illustrates an electrode emulation device 600 which includes the main unit 602 (including a signal generator/driver 610 and a switch assembly 620) connected to an electrode array 630. The device 600 includes means for evaluating the geometry/size of the crania of the subject and/or the position of the electrode array on the crania of the subject, such as anchoring points 650, 652, 654, 656, and 658. The anchoring points may be configured to provide information indicative of a relative distance/angle there between, and a geometry/size of the crania of the subject may be evaluated based on the distances/angles between the anchoring points. According to some embodiments, at least some of the anchoring points may be placed in specific positions on the crania of the subject, for example ears, forehead and others.

Figure 7:
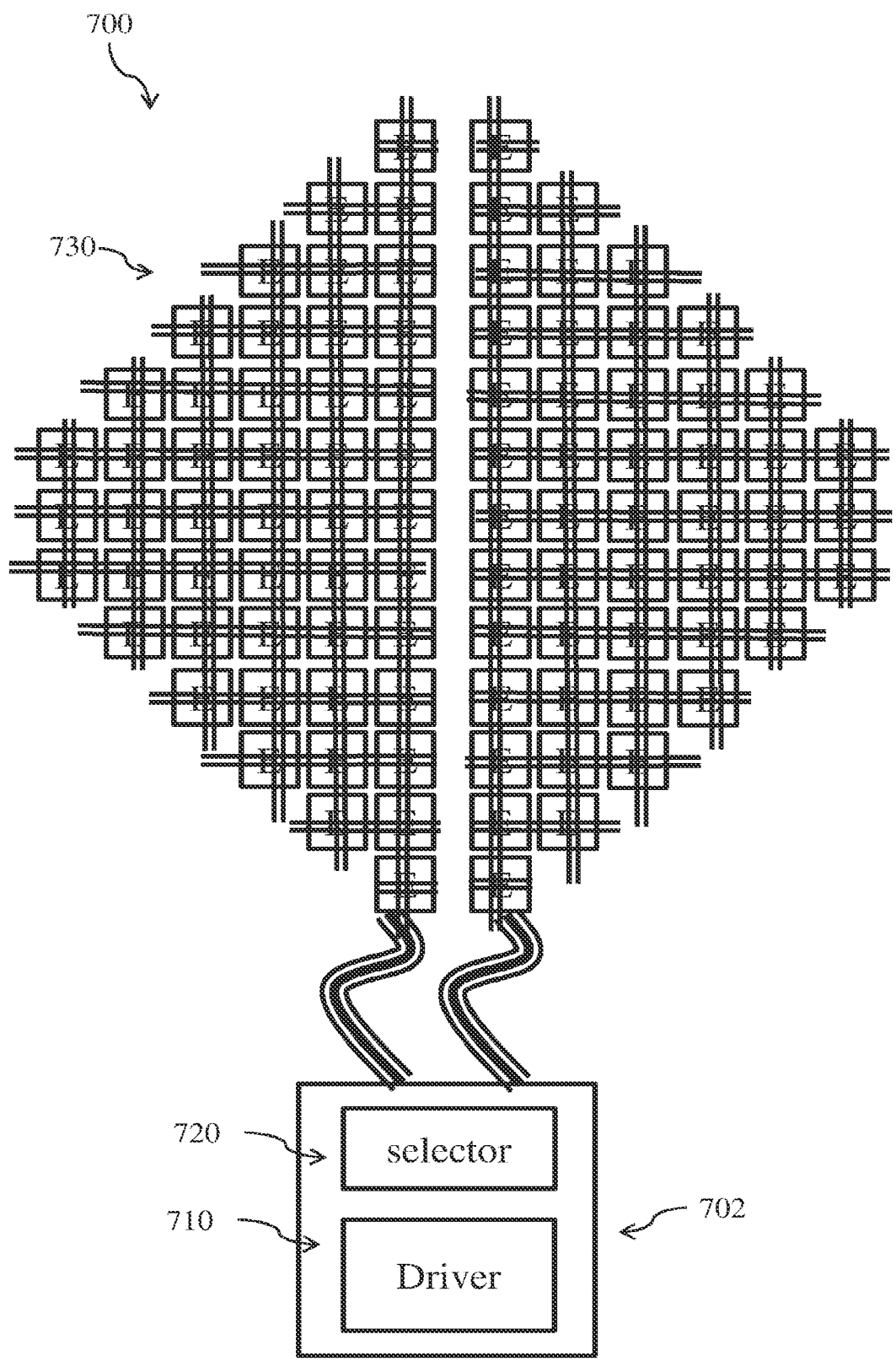
FIG. 7 schematically illustrates an electrode emulation device with array selection nets, according to some embodiments.

FIG. 7 more specifically exemplifies the embodiment of FIG. 2b with respect to the electrodes and switches arrangements in two groups associated with two drive ports. The figure schematically illustrates an electrode emulation device 700, in accordance with the invention. As shown in the figure, the electrodes together with their electrical connection lines form two stimulation nets, and a stimulation unit 702 includes a stimulation signal driver 710 configured to provide electric stimulation signal(s) to at least two stimulation nets, and a switching assembly 720 configured to operate the electrodes of electrode array 730 according to the selection performed by the controller and connect the selected electrodes to the at least two stimulation nets.

As described above, in various stimulation techniques, such as transcranial current stimulation or transcranial direct current stimulation, while stimulation may occur in regions in the vicinity of the anode(s), the regions near the cathode(s) are generally inhibited. To avoid such an undesired effect of the stimulation, the cathodes are commonly placed near regions where inhibition may not be of severe consequences. Especially in brain stimulation, there is a need for stimulating one brain region, while not suffering an unintended inhibition of a different region. Additionally, when electrodes are placed on the scalp of the user/subject to target an underlying brain region, there is generally a degree of uncertainty as to the exact location of the underlying target brain region. Thus, the stimulation does not always reach or cover the target region(s).

The invention provides for mitigating the risk of misplacement of electrodes and/or mitigating the undesired inhibition effect of cathodes (or undesired stimulation/excitation effect of anodes if cathodal inhibition is desired), by providing a novel technique for delivering electric stimulation, wherein the location(s) through-which the signal is provided to/collected from the body may change during the stimulation of a certain brain region(s). The inhibition effect of cathodal stimulation may be mitigated or cancelled if the stimulation does not last for more than a certain amount of time, such as two minutes, three minutes, four minutes, five minutes, six minutes or other times based on the location of the electrodes and characteristics of the stimulation signal.

As described above, in the system of the invention, a plurality of electrodes may be configured to define first and second effective sets of electrodes (each set having one or more electrode elements), such that a first effective set of electrode(s) is selected to form a first cluster of electrodes, and a second set of electrodes is selected to form a second cluster of electrodes. A stimulation signal may be delivered through the first cluster of electrodes and the second cluster of electrodes for a certain amount of time, and then the electrode selection of the first set (and/or the second set) are changed, while the stimulation signal is being delivered, to form a different area of contact with the body and stimulate another target region in the body. According to some embodiments, the electrode selection of the first and/or second electrode sets changes for driving the stimulation signal to/from a different location in the body of the user at/before a certain time period, thereby limiting the inhibition time of a region, and advantageously mitigating or removing the inhibition effect thereto. By this, steering/scanning of different brain regions can be performed in a controllable manner.

Figure 8:
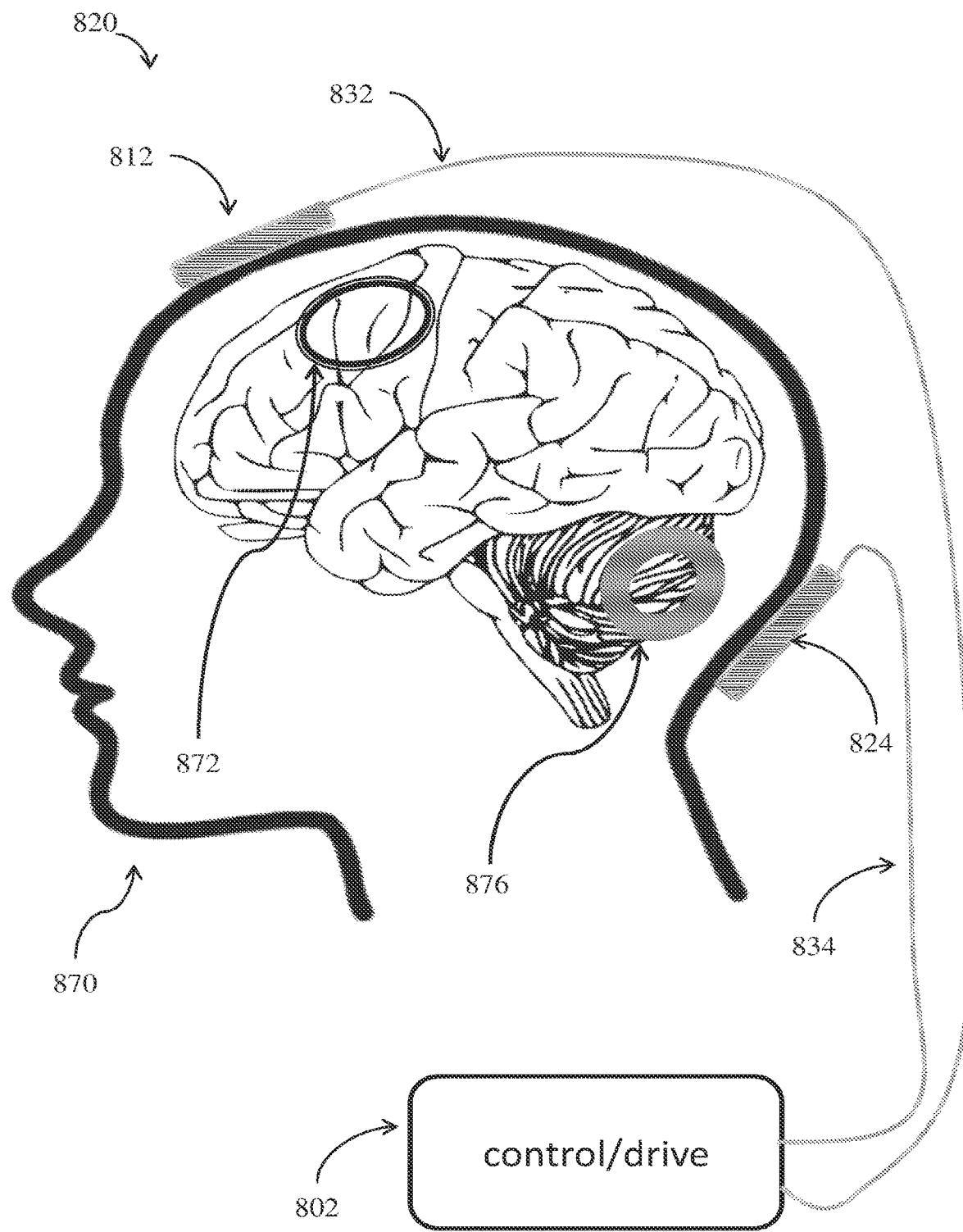
FIG. 8 schematically illustrates a common noninvasive electric brain stimulation setting.

Reference is made to FIG. 8, which schematically illustrates a conventional noninvasive electric brain stimulation system 820 having two single electrodes. Generally, an anode 812 is placed on the head of the user 870, near a target region 872 for stimulating it, and a cathode 824 is placed on a different region. A signal generator/driver 802 is connected to the anode 812 via an electric link such as anode wire 832, and to the cathode 824 via a cathode wire 834. There are two main problems with such system. First, the region 876 near cathode 824 is inhibited, and second, there is a degree of uncertainty as to the exact location of target region 872, in addition, there might be a misplacement of anode 812 that misses target region 872, or parts thereof.

Figure 9A:
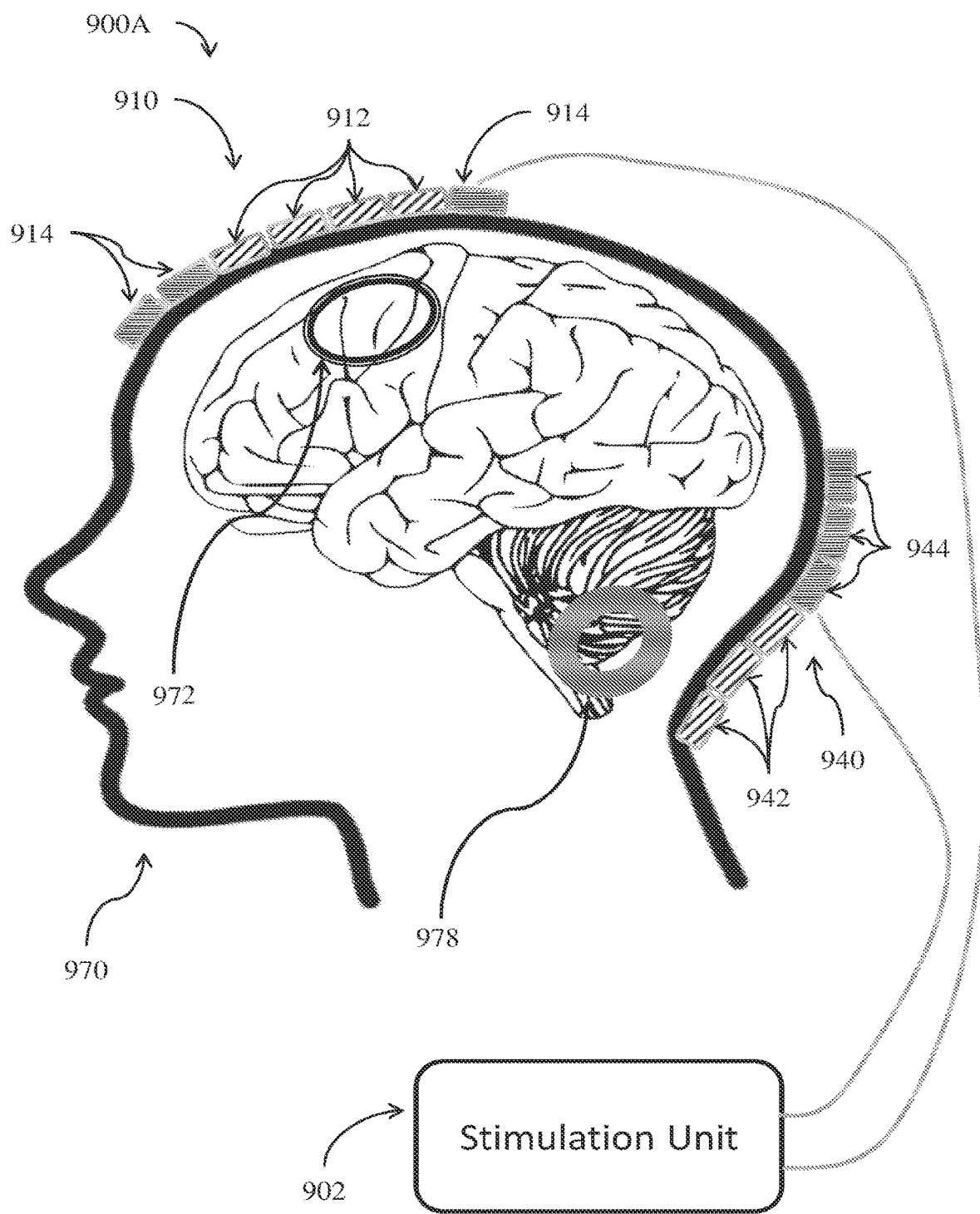
FIGS. 9a-b schematically illustrate a brain stimulation setting, according to some embodiments.
Figure 9B:
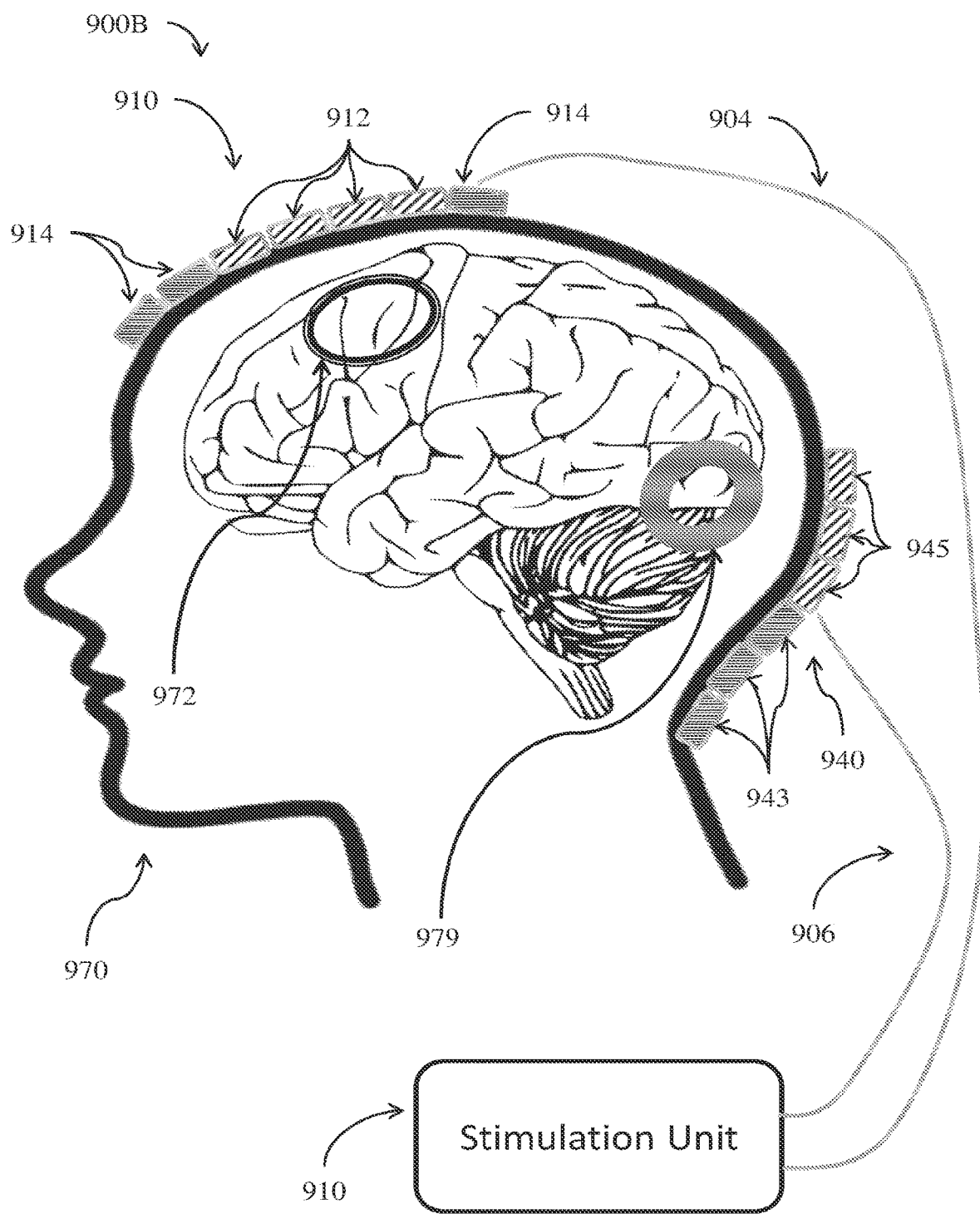

Reference is now made to FIGS. 9a-b, which schematically illustrate an example of a brain stimulation system, according to the invention. As shown, an anodal electrode array 910 and a cathodal electrode array 940 are placed on the body/head of the user 970, and are connected to a stimulation signal generator, such as signal driver 902, via anode-link 904 and cathode-link 906 respectively.

FIG. 9a depicts a first setting 900A of electrodes arrangement in accordance with the invention. The setting 900A is aimed at targeting the stimulation signal to reach target brain region 972. A set of electrodes 912 from anodal electrode array 910 is selected, while the rest of the electrodes 914 in the array are not selected. In the cathodal electrode array 940, a set of electrodes 942 are selected to close the electric loop for the stimulation signal, while the rest of the electrodes 944 are not selected. While providing stimulation in this configuration, the target region 972 is stimulated, while a brain region 978 close to the selected cathodal electrodes 942 may be inhibited.

FIG. 9b depicts a second setting 900B, wherein the same set of electrodes 912 from anodal electrode array 910 is selected, while the rest of the electrodes 914 in the array are not selected. On the other hand, the selection of electrodes within the cathodal electrode array 940 changes during the stimulation, such that, a different set of electrodes 945 are selected to close the electric loop for the stimulation signal, while the rest of the electrodes 943 in cathodal electrode array 940 are not selected. While providing stimulation in this configuration, the target region 972 is still stimulated, while a brain region 979 close to the selected cathodal electrodes 925 may be inhibited.

Therefore, for stimulating target brain region 972, an alteration of cathodal electrode array 920 selection occurs during stimulation, while the signal is still provided by the stimulation unit.

The selection alteration can be configured such that it occurs at a rate that would mitigate the inhibition of brain regions that are in close proximity to the cathodes, e.g. regions 978 and 979 in this example. The alteration can be configured to occur after no longer than a predetermined period of time during stimulation, or after a random or pseudo random period of time during the stimulation. Specifically, the alteration can be configured to occur during the stimulation after no longer than 8, 7, 6, 5, 4, 3, 2 or 1 minutes from the beginning of the stimulation, or the previous selection alteration, the decision about the time limit period for performing the selection alteration may depend on the subject's specific parameters, such as age, gender, diagnosis and cognitive ability, head impedance and the like.

Figure 10A:
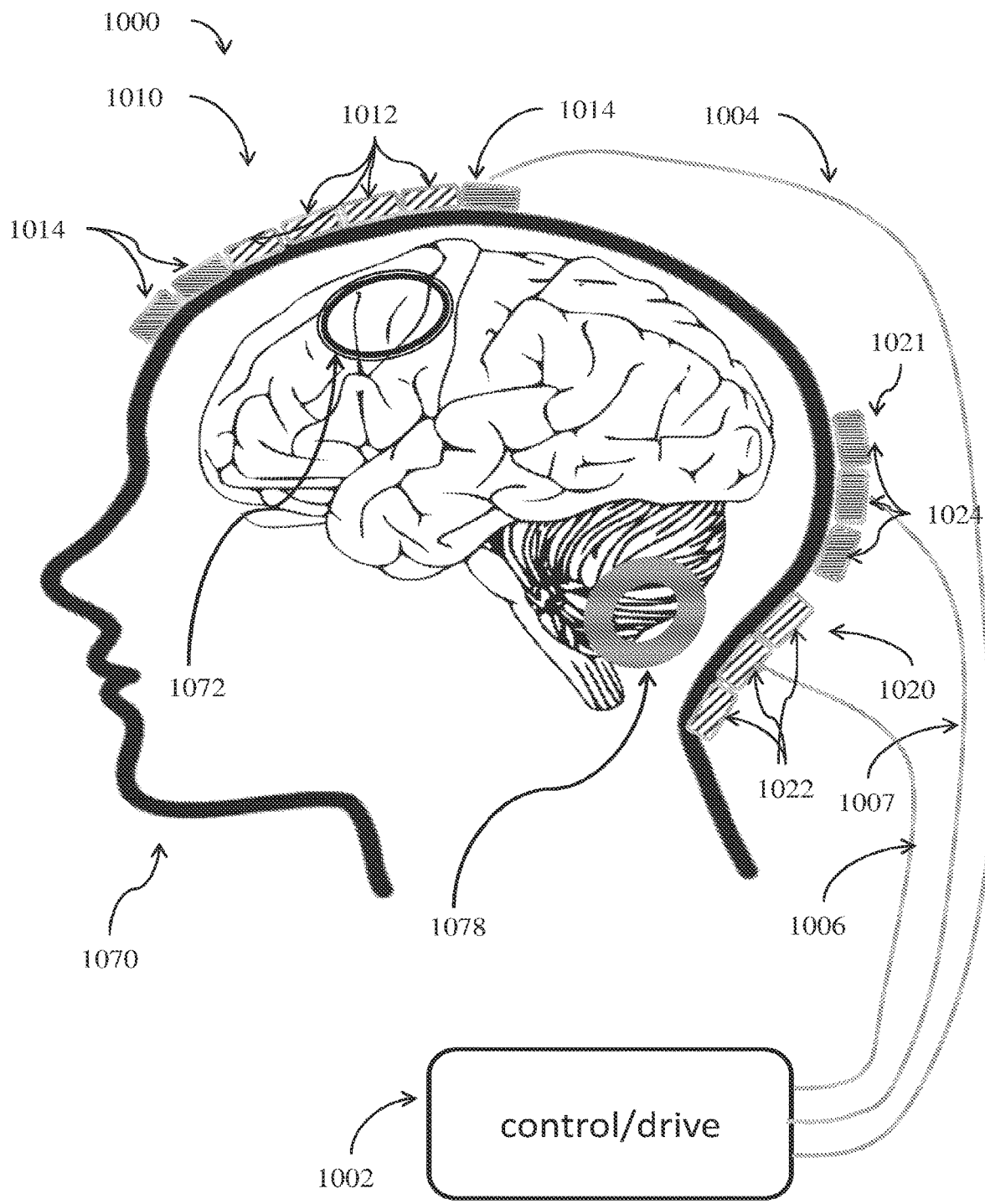
FIGS. 10a-b schematically illustrate a brain stimulation setting, according to some embodiments.
Figure 10B:
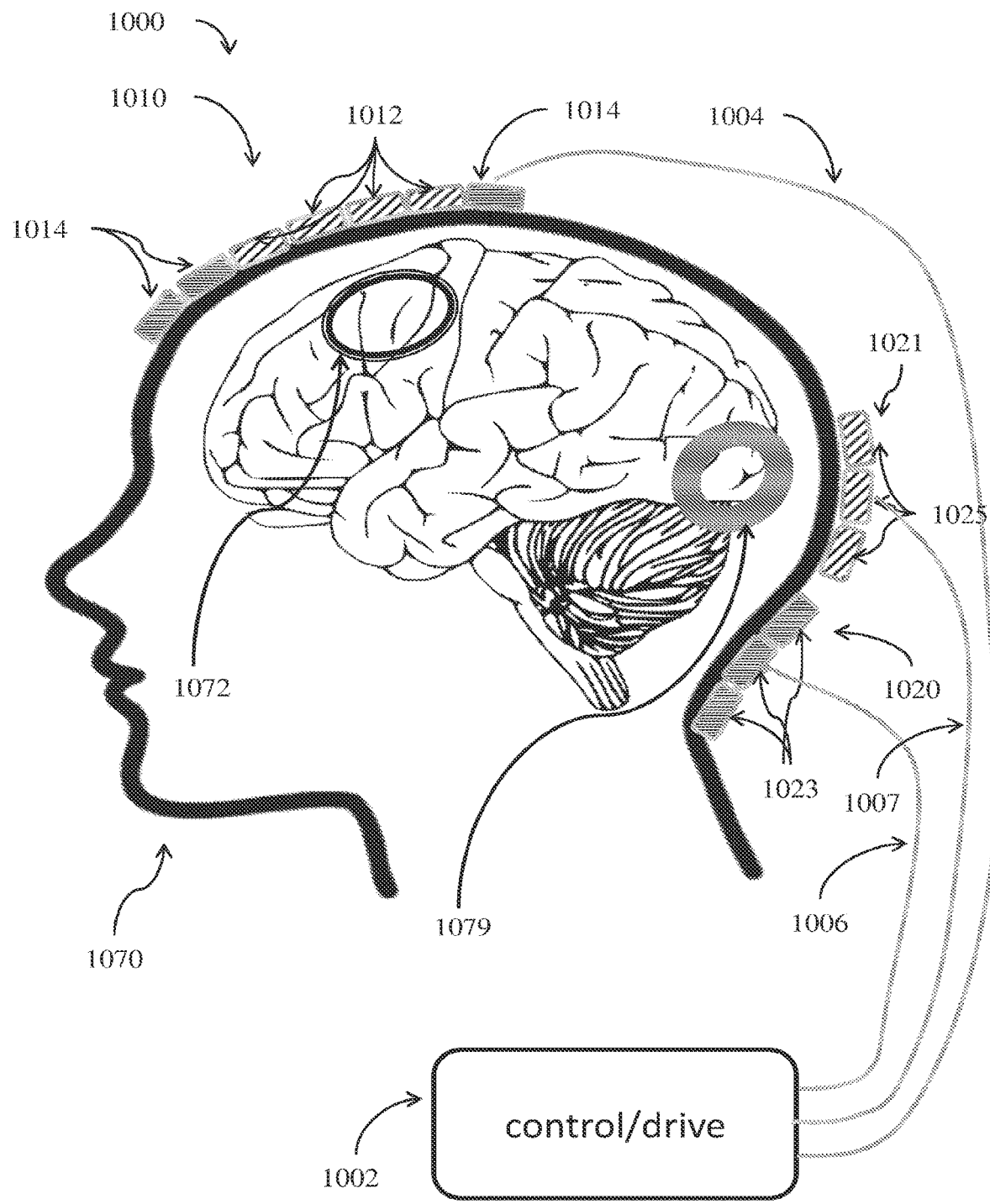

Reference is now made to FIGS. 10a-b, which schematically illustrate another example of a brain stimulation system 1000, according to the invention. In this example, three groups/arrays of electrodes are placed on the head/scalp 1070 of the participant/user, anodal array 1010, first cathodal array 1020 and second cathodal array 1021, each configured to have electrodes therein being controllably associated with the signal generator 1002 for providing a stimulation signal transmitted via anodal signal link 1004, and collected via first cathodal signal link 1006 and second cathodal signal link 1007.

In FIG. 10a, a set of anode electrodes 1012 of the anodal array 1010 are selected to be electrically associated with signal generator 1002 for providing the stimulation signal to target brain region 1072, while the rest of the electrodes 1014 in the anodal array 1010 are not selected. Electrodes 1022 of the first cathodal array 1020 are selected to be electrically associated with signal generator 1002 for completing the electric loop of the stimulation signal, thereby affecting first nontarget brain region 1078, for a first time interval/duration, while electrodes 1024 of the second cathodal array 1021 are not selected.

In FIG. 10b, after the first time interval/duration ends, the selection in the anodal array 1010 stays unchanged, with the set of anode electrodes 1012 being selected to be electrically associated with signal generator 1002 for providing the stimulation signal to target brain region 1072, while the rest of the electrodes 1014 in anodal array 1010 are not selected. An alteration in the cathode electrodes is made such that electrodes 1025 of the second cathodal array 1021 are selected to be electrically associated with signal generator 1002 for completing the electric loop of the stimulation signal, while electrodes 1023 of the second cathodal array 1020 are not selected, thereby affecting second nontarget brain region 1079, for a second time interval/duration.

The first cathodal array 1020, the second cathodal array 1020 and/or the anodal array 1010 can include one electrode each, and then the selection is between one electrode placed at a certain region, and another electrode placed at a different region.

Generally, the exact location of the target brain region may not be known at a very high certainty, therefore, one approach may be to use an effective electrode that is larger than the surface area of the target brain region, thereby raising the probability of targeting the target brain region with the stimulation signal, but this approach reduces the flux of current density delivered to the target brain region. Alternatively, one may use a smaller effective electrode to achieve the desired current density, but this may reduce the probability of targeting the target brain region or parts thereof.

According to some embodiments, the system is configured to permit stimulation with a current density of up-to 14.3 $mA/cm^2$, approximately 1 $mA/cm^2$, approximately 0.1 $mA/cm^2$, approximately 0.01 $mA/cm^2$, based on the age, gender, skin condition, electrode size and type, target region or other related criteria.

Thus, according to the invention there are provided systems, devices and methods for targeting a stimulation signal to a target brain region with location uncertainty, by providing a signal to regions with higher location certainty at higher intensities during a stimulation session, while providing a signal to regions with lower location certainty at lower intensities during a stimulation session.

Additionally, there are provided systems, devices and methods for targeting a stimulation signal to a target brain region with location uncertainty, by providing a signal to regions with higher location certainty for longer duration(s) during a stimulation session, while providing a signal to regions with lower location certainty for shorter duration(s) during a stimulation session.

Figure 11A:
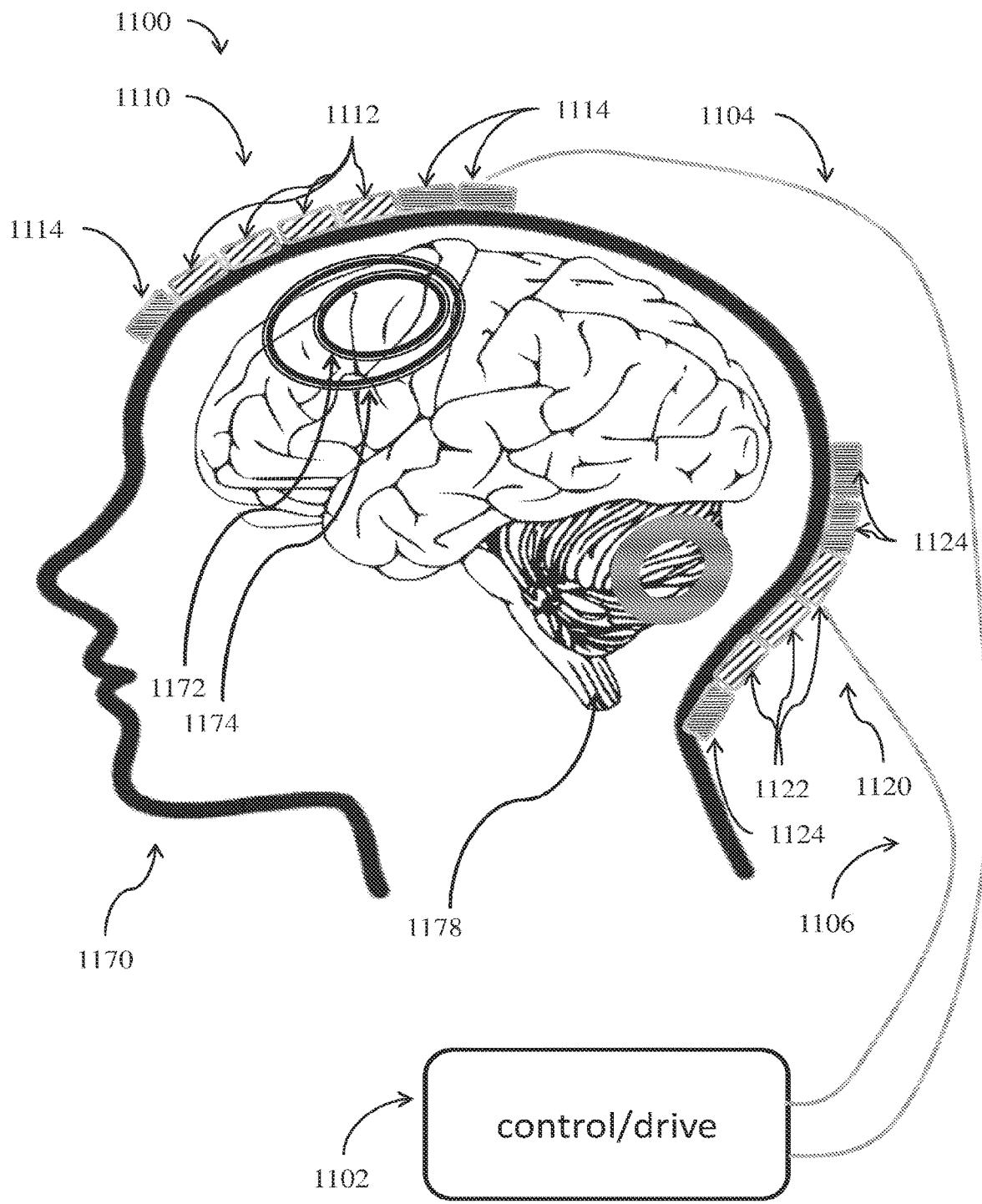
FIGS. 11a-b schematically illustrate a brain stimulation setting, according to some embodiments.
Figure 11B:
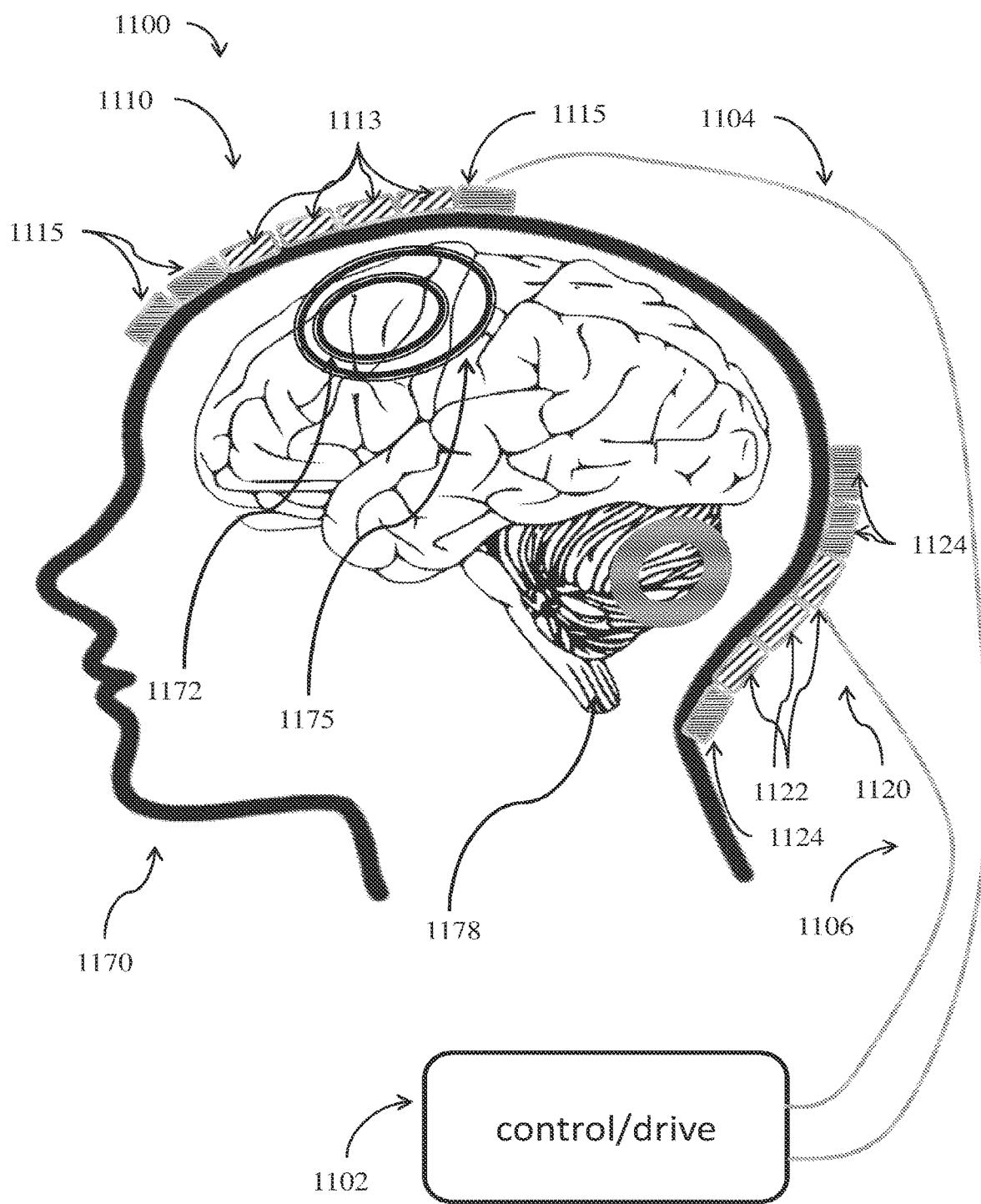

Reference is now made to FIGS. 11a-b, which schematically illustrate a brain stimulation system 1100, according to the invention. As shown, an anodal array 1110 and a cathodal array 1120 are provided and placed on the user 1170, and are configured to have at least some of the electrodes therein to be electrically associated with a stimulation signal generator 1102 via first signal link 1104 and second signal link 1106 respectively.

In FIG. 11a, a first set of electrodes 1112 in the anodal array 1110 are selected to be electrically associated with the stimulation signal generator 1102, while the rest of anode electrodes 1114 are not selected, to thereby affect stimulation to high-certainty target region 1172, and a first low certainty brain region 1174 for a first time interval/duration. Additionally, a set of cathode electrodes 1122 are selected to utilize a closure of the electric signal circuit through user 1170, while the rest of the cathode electrodes 1124 are not selected, affecting drain-brain region (nontarget brain region) 1178. It is desired to provide stimulation to high-certainty brain region 1172 at higher intensity and/or longer time duration than lower-certainty brain region 1174. Therefore, during stimulation and after a certain time period, the selection of electrodes in the anodal array 1110 is changed such that high-certainty brain region is still targeted, and low-certainty brain region 1174 is not targeted any longer. This is shown in FIG. 11b, showing that the selection of anode electrodes is changed, and a second set of electrodes 1113 in the anodal array 1110 are selected to be electrically associated with stimulation signal generator 1102, while the rest of the anode electrodes 1115 are not selected, to thereby affect stimulation to high-certainty target region 1172, and second low certainty brain region 1175 for a second time interval/duration. In the meanwhile, the cathode electrode selection may be unchanged, and cathode electrode set 1122 may still be selected to utilize a closure of the electric signal circuit through user 1170, while the rest of cathode electrodes 1124 are not selected, thereby affecting drain-brain region (nontarget brain region) 1178.

The electrodes or electrode array may include a plurality of electrodes each, thereby providing selection ability within a group of electrodes for fine stimulation/inhibition of the target/nontarget region.

Figure 12A:
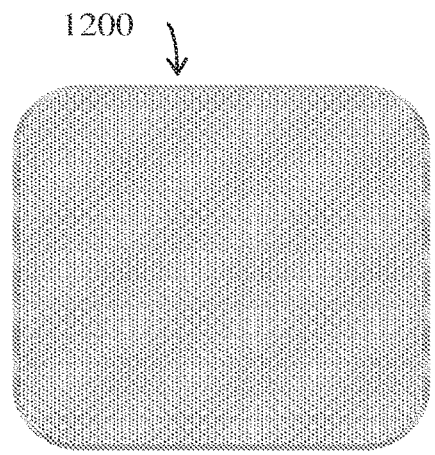
FIGS. 12a-c schematically illustrate electrode groups, according to some embodiments.
Figure 12B:
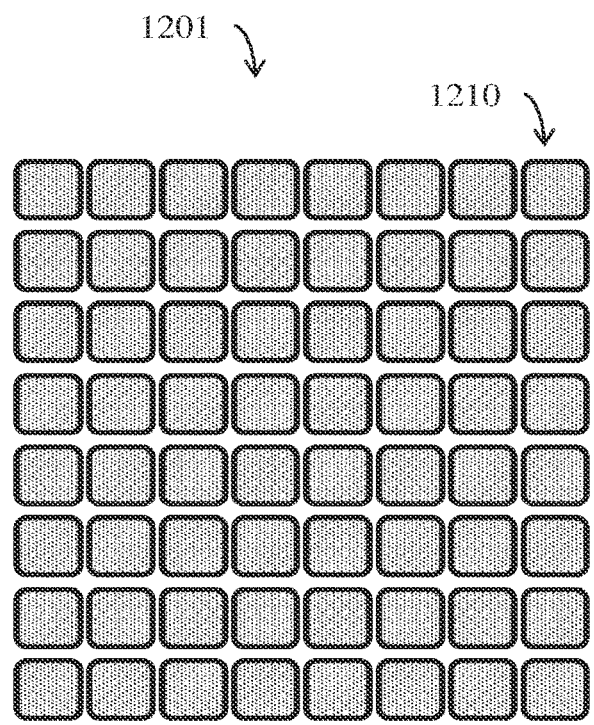
Figure 12C:
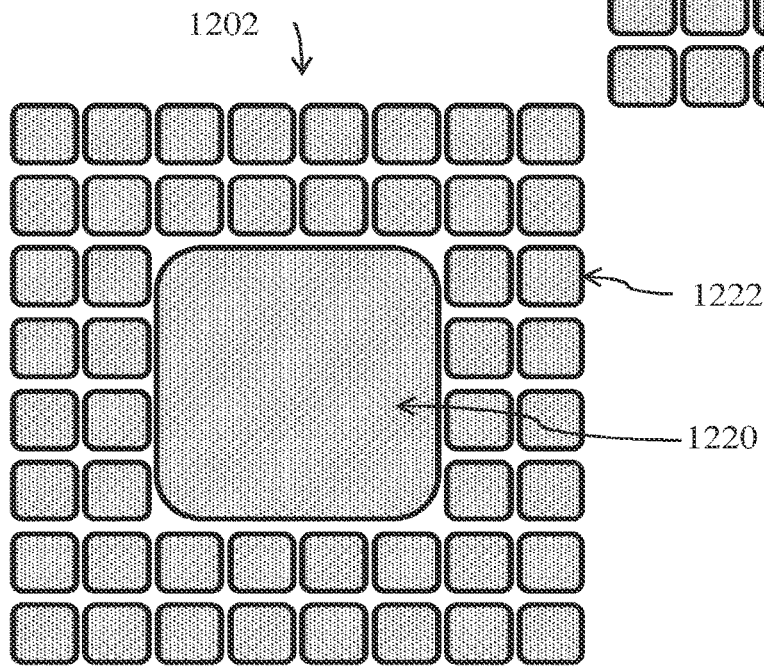

Reference is now made to FIGS. 12a-c, which schematically illustrate electrode groups, according to some embodiments of the invention. All of embodiments can be used for spatial and/or temporal control of the stimulation signal by suitable selection of the active and inactive electrodes in the groups.

FIG. 12a, illustrates a single electrode 1200, which is configured to be placed on the crania/scalp/head of the user to provide stimulation/inhibition to an underlying/close brain region. This electrode does not allow selection of smaller sub-electrodes for adjustment of shape and position.

FIG. 12b, illustrates an array 1201 of multiple electrodes 1210 which are roughly identical in area, and are arranged to provide a sufficient resolution of selection to emulate a location, shape, and size of a larger electrode. A change in electrode selection within the array 1201 of electrodes 1210 can be utilized for example for changing the location on the scalp of the user through which the stimulation signal is provided or retained/taken.

FIG. 12c, illustrates an array of electrodes 1202, having one or more main electrode(s) 1220, and a plurality of "adjustment" electrodes 1222. This configuration may be useful when a location at the center of electrodes 1202 is of high certainty, and adjustment of electrode selection may be required in the peripherals thereof.

According to some embodiments, the sub-electrodes in an array/arrangement of electrodes are shaped and arranged to provide a spatial resolution (for electrode selection) of at least 2 cm in each direction. The spatial resolution in each direction may be at least 1 cm, or generally, at least x cm, wherein x is determined based on the application, target region selectivity, and the like. It should be understood that in order to enable creation of as many variations as possible for the electric field profile parameters (achieving an accurate emulation of electrodes' shape and size, as well as for a more accurate positioning emulation), it is desirable to have as higher as possible spatial resolution for stimulation points defined by the sub-electrodes.

The spatial resolution is determined by the size and shape of sub-electrodes in the array/arrangement, as well as the distance between adjacent sub-electrodes, such as center-to-center distance (pitch), and edge-to-edge distance.

According to some embodiments, the center-to-center distance between adjacent sub electrodes is up to 3 cm, e.g. up to 2 cm, up to 1.5 cm, or up to 1 cm.

According to some embodiments, the edge-to-edge distance between adjacent sub electrodes is up to 10 mm, e.g. up to 5 mm, up to 3 mm, up to 2 mm, or up to 1 mm.

For achieving effective emulation, it is desired to keep the contact area of the aggregate of the selected sub-electrodes as close as possible to the emulated electrode, and within the perimeters thereof. As a result, it is advantageous to design the sub electrodes to have a higher "active area" (conductive members/regions) to "dead area" (isolative/non-conductive members/regions). In other words, the fill factor of the "active area" defined by the surface area of sub-electrodes (or electrode elements) is much higher than a that of "dead area" defined by the surface area of the spaces between the sub electrodes.

As used herein, the term "spatial-efficiency" refers to the ratio between the actual area of selected sub-electrodes within a desired emulated electrode (which is virtual), and the total area of the virtual desired emulated electrode.

According to some embodiments, the spatial-efficiency of an electrode arrangement is at least 30%. According to some embodiments, the spatial-efficiency of an electrode arrangement is at least 40%, at least 50%, at least 60%, at least 70%, at least 80%, or at least 90%.

According to some embodiments, the ratio between the active area and dead area of electrodes is greater than 30%. According to some embodiments, the ratio between the active area and dead area of electrodes is greater than 50%, greater than 60%, or greater than 70%.

Reference is now made to FIGS. 13a-e, which schematically illustrate electrode set selection of an electrode array 1300, that includes a plurality of co-centric, or semi-co-centric electrodes, such as central electrode 1302, middle electrode 1304, and external electrode 1306. The selection of any possible combination within the electrode array 1300 may be available for reaching the stimulation pattern or location altering required. In the figures, some non-limiting examples are shown.

FIG. 13a illustrates a setting of the electrode array 1300, wherein none of central electrode 1302, middle electrode 1304 nor external electrode 1306 is selected. FIG. 13b illustrates a setting of the electrode array 1300, wherein central electrode 1302 is selected, while middle electrode 1304 and external electrode 1306 are not selected. FIG. 13c illustrates a setting of the electrode array 1300, wherein central electrode 1302 and middle electrode 1304 are selected, while external electrode 1306 is not selected. FIG. 13d illustrates a setting of the electrode array 1300, wherein central electrode 1302, middle electrode 1304 and external electrode 1306 are all selected. FIG. 13e illustrates a setting of the electrode array 1300, wherein central electrode 1302 is not selected, while middle electrode 1304 and external electrode 1306 are selected.

Reference is now made to FIGS. 14a-e, which schematically illustrate electrode set selection of an electrode array 1400 which includes a central electrode 1401, and peripheral surrounding electrodes, such as top electrode 1402, left electrode 1403, bottom electrode 1404 and right electrode 1405. The selection scheme can be such that different electrodes are selected at different times in an exclusive manner, such that different sets of electrodes with no shared sub-electrodes are selected at a certain time interval. In the figures, some non-limiting examples are shown.

Figure 14A:
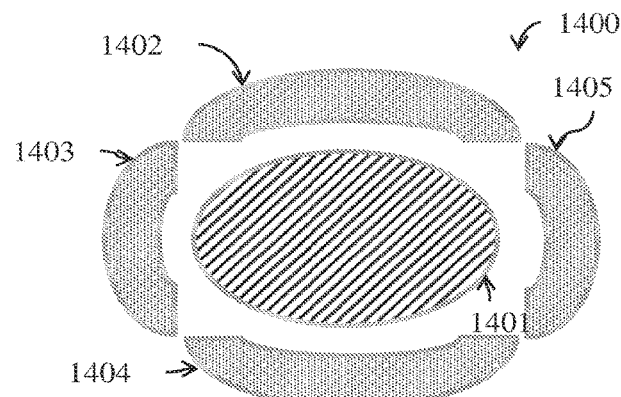
FIGS. 14a-e schematically illustrate electrode set selection of an array of electrode, according to some embodiments.
Figure 14B:
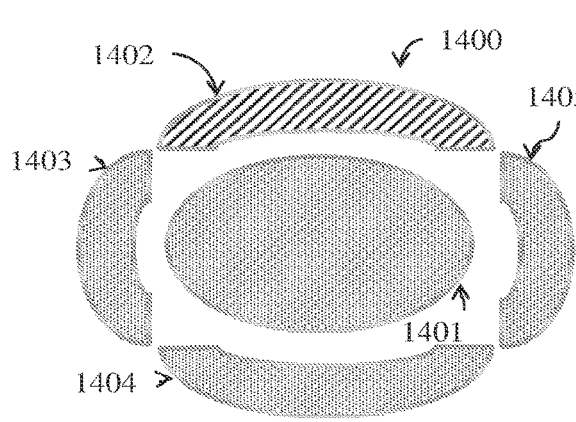
Figure 14C:
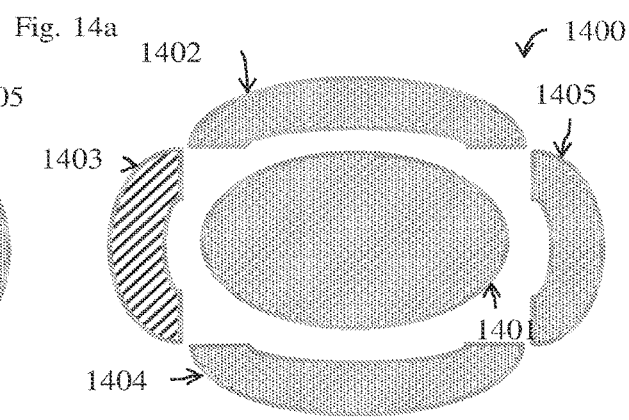
Figure 14D:
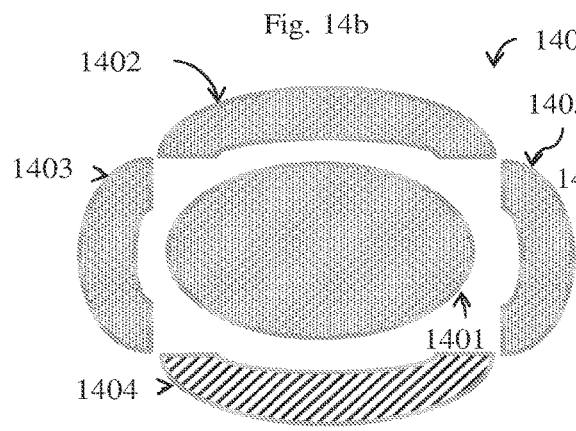
Figure 14E:
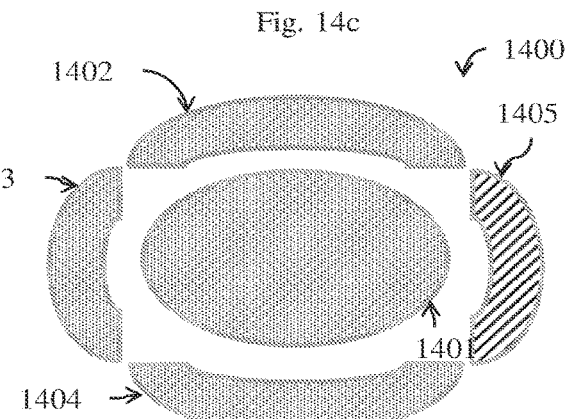

FIG. 14a illustrates a setting of the electrode array 1400, wherein central electrode 1401 is selected, while top electrode 1402, left electrode 1403, bottom electrode 1404, and right electrode 1405 are not selected. FIG. 14b illustrates a setting of the electrode array 1400, wherein top electrode 1402 is selected, while central electrode 1401, left electrode 1403, bottom electrode 1404, and right electrode 1405 are not selected. FIG. 14c illustrates a setting of the electrode array 1400, wherein left electrode 1403 is selected, while central electrode 401, top electrode 1402, bottom electrode 1404, and right electrode 1405 are not selected. FIG. 14d illustrates a setting of the electrode array 1400, wherein bottom electrode 1404 is selected, while central electrode 1401, top electrode 1402, left electrode 1403, and right electrode 1405 are not selected. FIG. 14e illustrates a setting of the electrode array 1400, wherein right electrode 1405 is selected, while central electrode 1401, top electrode 1402, left electrode 1403, and bottom electrode 1404 are not selected.

Reference is now made to FIGS. 15a-e, which schematically illustrate electrode set selection of an electrode array 1500 which includes a central electrode 1501, and peripheral surrounding electrodes, such as top electrode 1502, left electrode 1503, bottom electrode 1504 and right electrode 1505. The selection scheme can be such that different electrodes are selected at different times in an exclusive, mutually exclusive, semi-exclusive or semi-mutually exclusive manner.

Figure 15A:
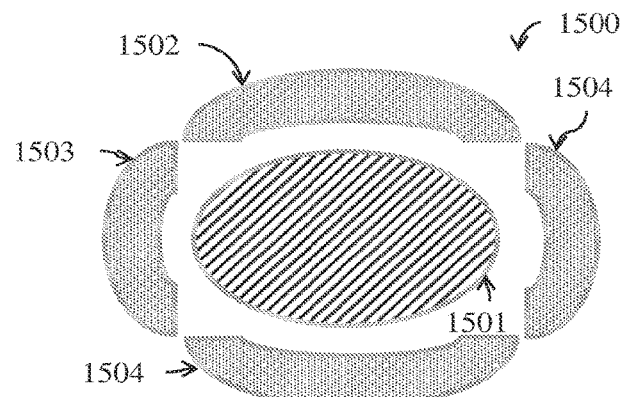
FIGS. 15a-e schematically illustrate electrode set selection of an array of electrode, according to some embodiments.
Figure 15B:
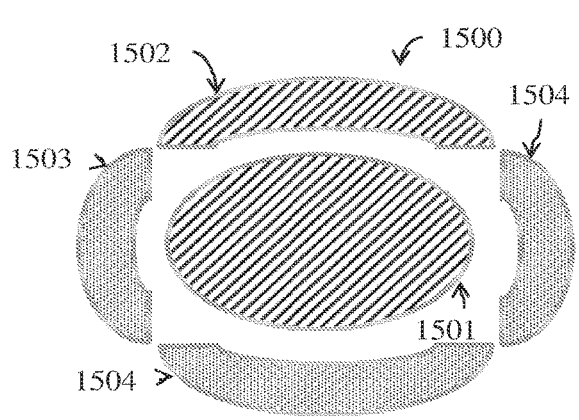
Figure 15C:
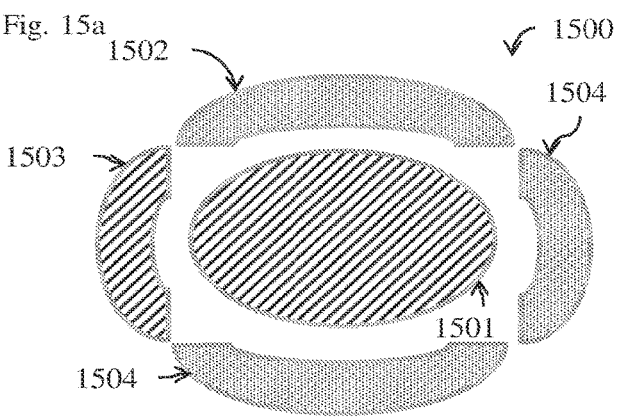
Figure 15D:
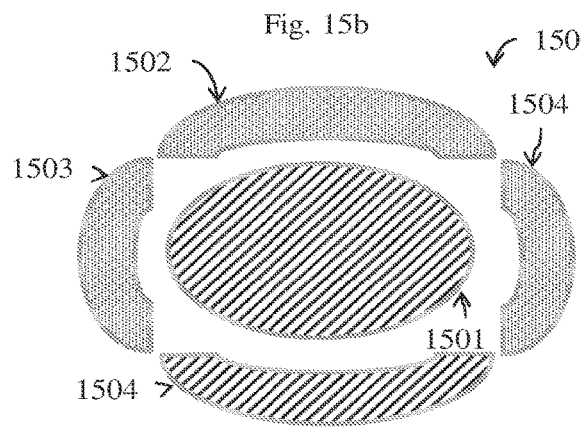
Figure 15E:
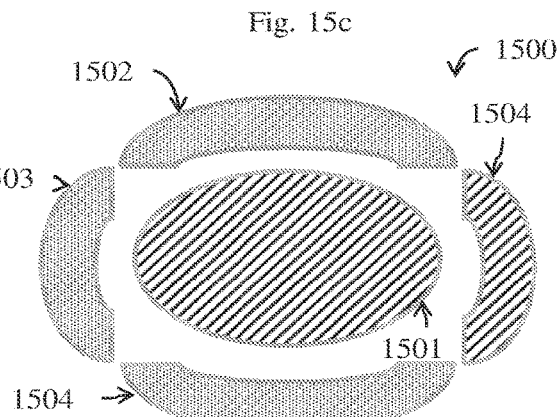
Figure 16A:
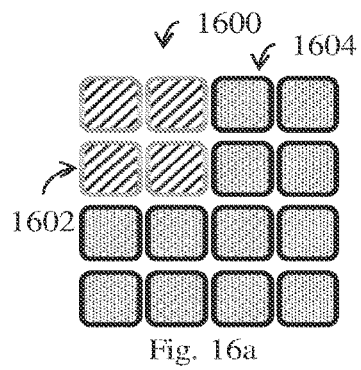
FIGS. 16a-i schematically illustrate electrode set selection of an array of electrode, according to some embodiments.
Figure 16B:
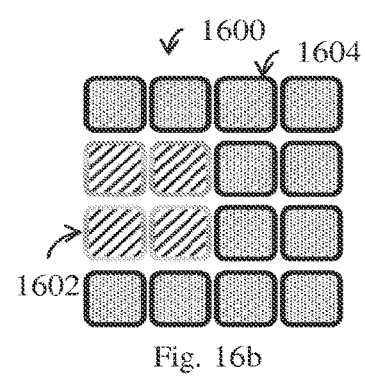
Figure 16C:
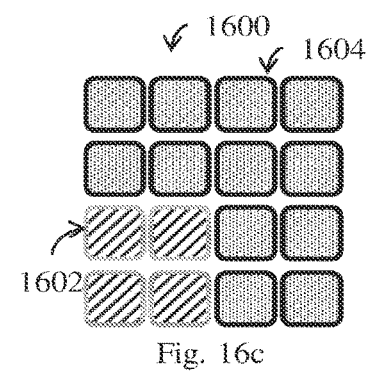
Figure 16D:
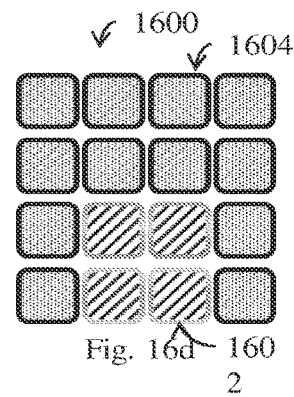
Figure 16E:
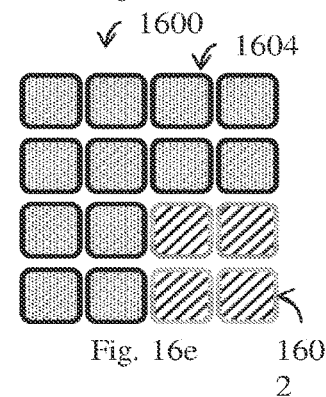
Figure 16F:
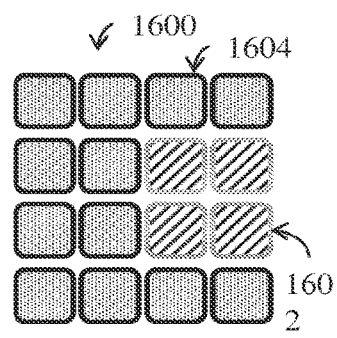
Figure 16G:
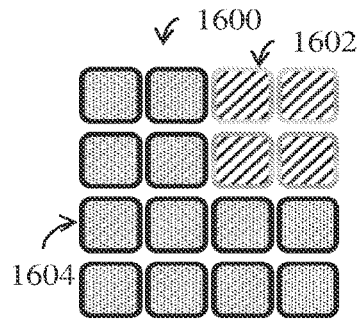
Figure 16H:
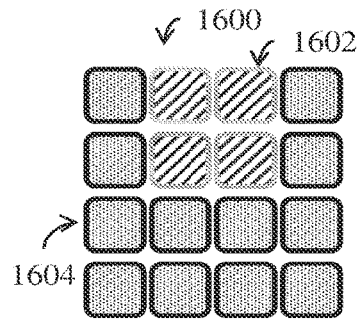
Figure 16I:
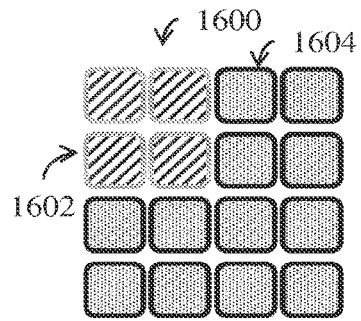

FIG. 15a illustrates a setting of the electrode array 1500, wherein central electrode 1501 is selected, while top electrode 1502, left electrode 1503, bottom electrode 1504, and right electrode 1505 are not selected. FIG. 15b illustrates a setting of the electrode array 1500, wherein central electrode 1501 and top electrode 1502 are selected, while left electrode 1503, bottom electrode 1504, and right electrode 1505 are not selected. FIG. 15c illustrates a setting of the electrode array 1500, wherein central electrode 1501 and left electrode 1503 are selected, while top electrode 1502, bottom electrode 1504, and right electrode 1505 are not selected. FIG. 15d illustrates a setting of the electrode array 1500, wherein central electrode 1501 and bottom electrode 1504 are selected, while top electrode 1502, left electrode 1503, and right electrode 1505 are not selected. FIG. 15e illustrates a setting of electrode array 1500, wherein central electrode 1501 and right electrode 1505 are selected, while top electrode 1502, left electrode 1503, and bottom electrode 1504 are not selected.

As mentioned above, the selection characteristics, such as the selection scheme/pattern, the selection alteration duration (transition, fade in and fade out between selections), the duration of a certain electrode selection and more, are configurable and/or can be based on certain criteria and/or the desired effect to be achieved The transition between one selection to another can be such that there are no common electrode selections between the different phases or such that at least some electrodes are selected in different phases.

Reference is now made to FIGS. 16a-i, which schematically illustrate electrode set selection of an electrode array 1600. As illustrated, at least some of the electrodes are selected 1602, while the others are nor selected 1604. The electrode selection can emulate a "hovering" of a bigger electrode in the region of electrode array 1600. FIGS. 16a-i illustrate a counter-clockwise hovering of 4 selected electrodes, such that between each two adjacent selection phases, at least one, or as illustrated, two, electrodes are shared.

The electrode selection changes can be done such that the flux or current density is maintained roughly unchanged between the phases. This can be achieved by maintaining the same signal current value and the same effective surface area between two selection changes. Alternatively, this may be achieved by changing the current value of the signal at a ratio equal to the ratio of the change in electrode effective surface area between two selection phases.

According to the invention, an electrode array can include any number of electrodes, as the specific application requires. For example, the electrode array can include 1, 2, 3, 4, 5, 8, 16, 32, 64, 128, 256, 512, 1024, or 2048, or even more electrodes.

According to the invention, the effective area of the electrode array can be approximately 1 cm$^2$, approximately 2 cm$^2$, approximately 3.14 cm$^2$, approximately 5 cm$^2$, approximately 10 cm$^2$, approximately 25 cm$^2$, approximately 35 cm$^2$, or approximately 70 cm$^2$ or more.

Figure 17:
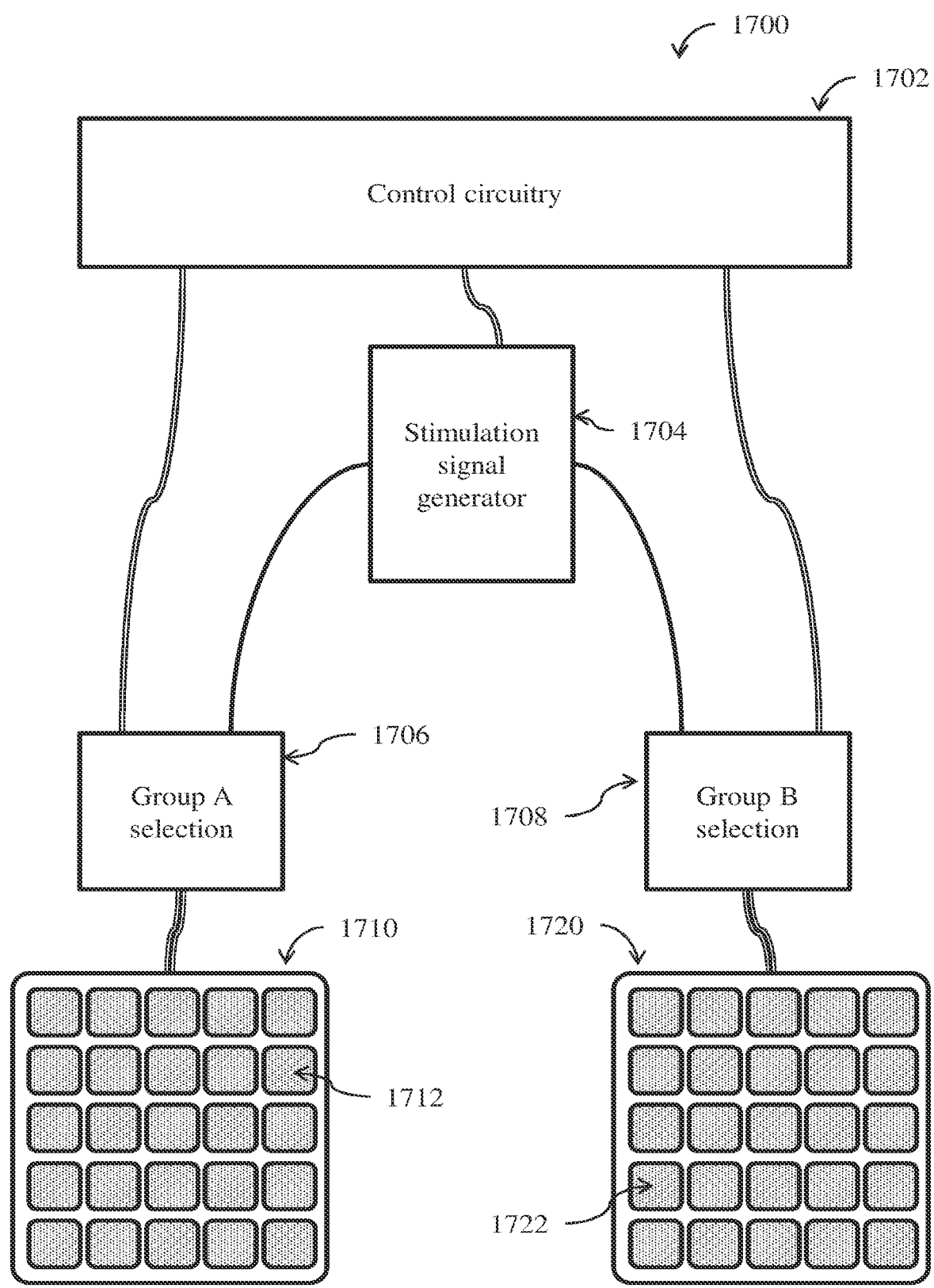
FIG. 17 schematically illustrates a stimulation system with two groups of electrode arrays, according to some embodiments.

Reference is now made to FIG. 17, which schematically illustrates a stimulation system 1700 with two groups of electrode arrays, electrode array 1710 and electrode array 1720. The stimulation system 1700 includes a control circuitry 1702, which is configured to control a stimulation signal generator 1704, a group selector 1706 for selection of electrodes 1712 from electrode array 1710, and a group selector 1708 for selection of electrodes 1722 from electrode array 1720.

Figure 18:
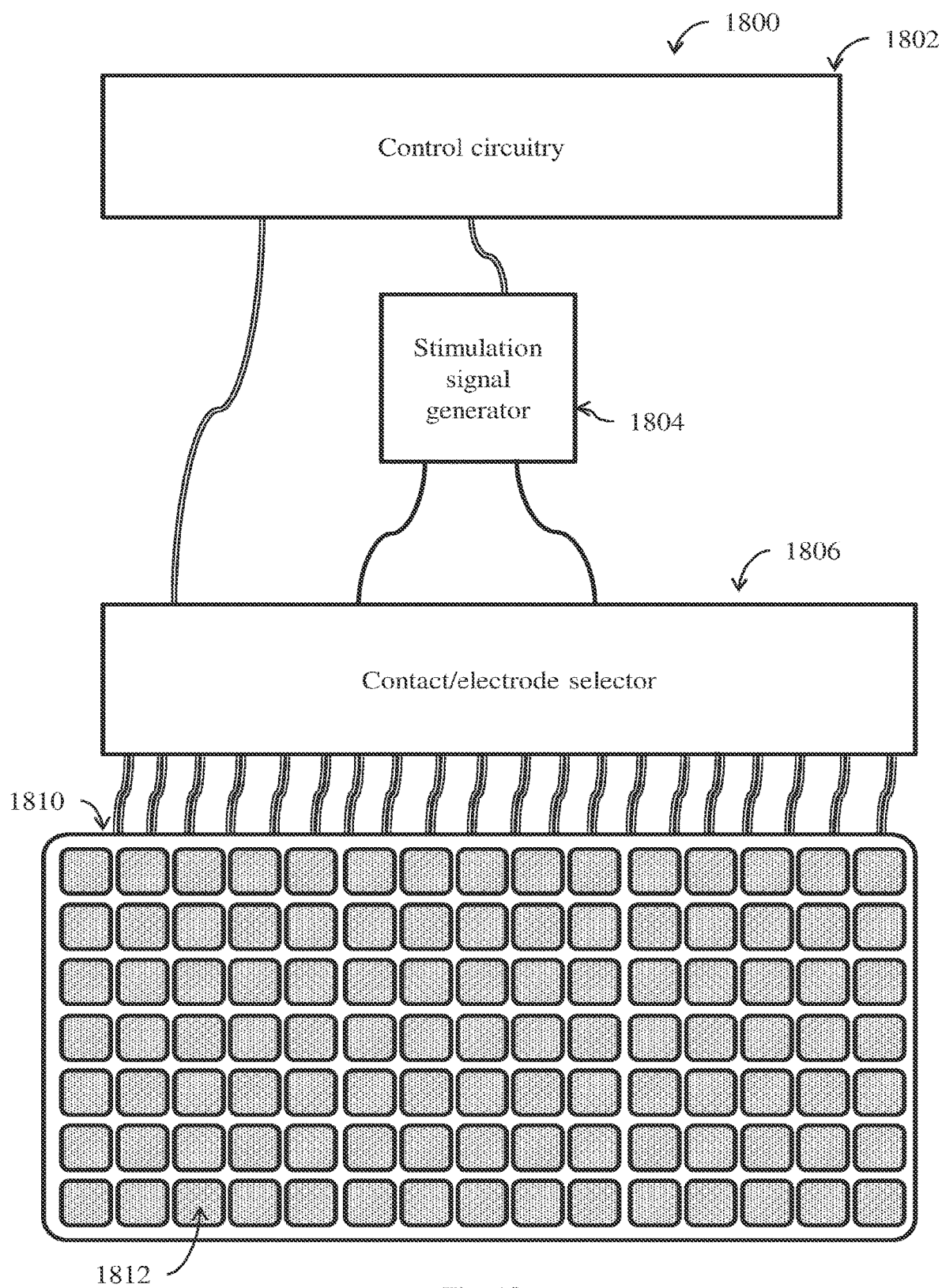
FIG. 18 schematically illustrates a stimulation system with an array of many electrodes, according to some embodiments.

Reference is now made to FIG. 18, which schematically illustrates a stimulation system 1800 with a multi-electrode array 1810. The system 1800 includes a control circuitry 1802 which is configured to control a stimulation signal generator 1804 to determine stimulation signal properties, such as intensity, duration, frequency, technique (tDCS, tRNS, tACD or the like). Control circuitry 1802 is further configured to determine the selection of electrodes 1812 within multi-electrode array 1810 by controlling a contact/electrode selector 1806, to achieve electrode positioning and electrode position adjustment, electrode position change (hovering) and/or change of electrode positions for stimulating/inhibiting a different target brain region.

Figure 19:
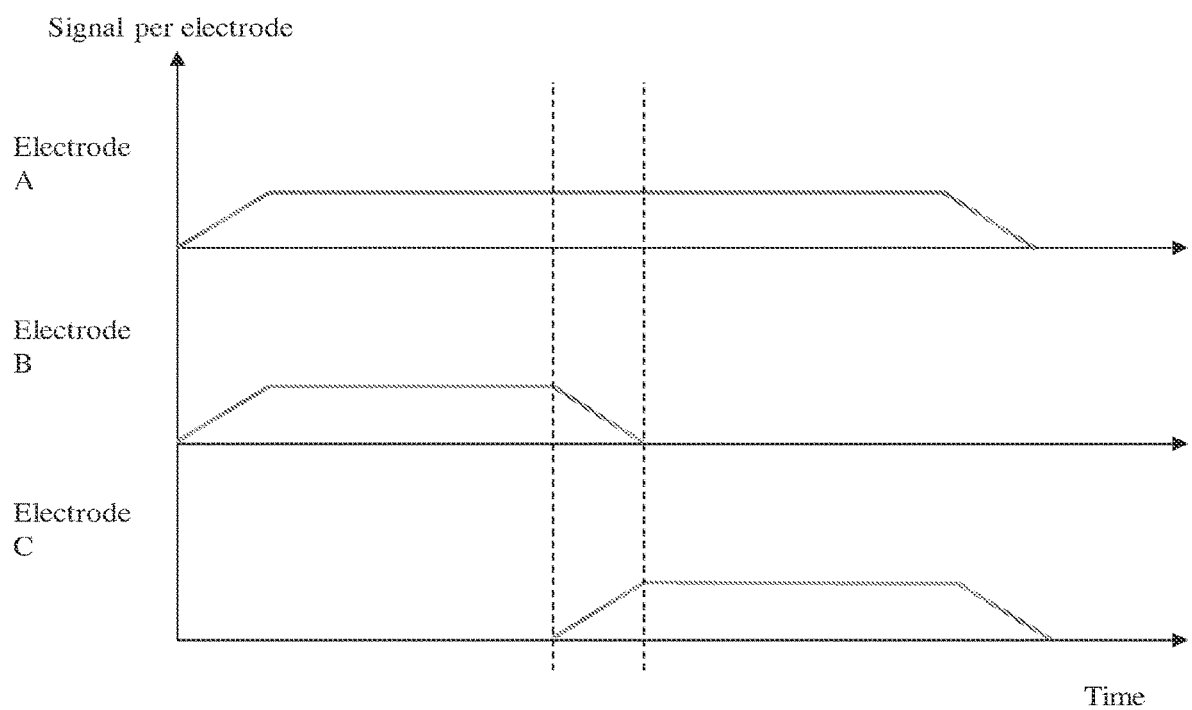
FIG. 19 schematically illustrates a stimulation time illustration, according to some embodiments.

Reference is now made to FIG. 19, which schematically illustrates a non-limiting example of stimulation time of different effective electrodes. As illustrated, while the selection of electrode A is maintained (with a fade in and a fade out activation), there is an alteration in the selection between electrode B and electrode C. During the transition phase of the selection, the current or signal intensity of electrode B fades out/ramps down, while the current or signal intensity of electrode C fades in/ramps up. The ramp down of electrode B and ramp up of electrode C can be such that the overall signal intensity is maintained. Advantageously, fading in and out between selections may reduce or eliminate undesired effects, such as a tingling effect or a burning effect.

It should be understood that, in some applications, there might be a need to successively stimulate different targets in the region of interest in different stimulation sessions. This can be done as described above and electronically (via switches) change the activated electrodes or electrode groups, thereby changing the effective electrode shape/size and location. Such re-switching can be controllably operable to meet the duration of each stimulation session.

Figure 20:
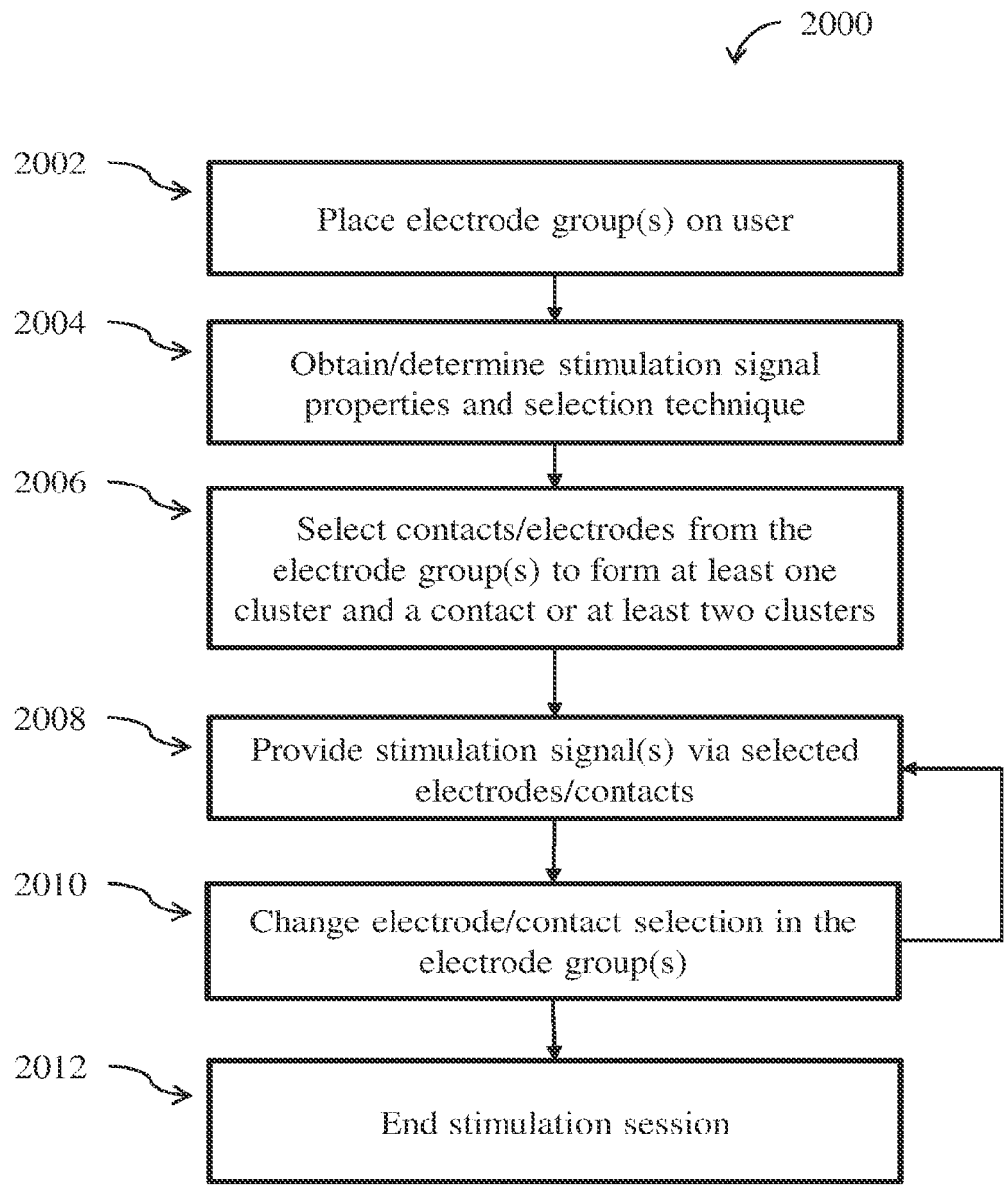
FIG. 20 schematically illustrates a method for multi-region brain stimulation, according to some embodiments.

Reference is now made to FIG. 20, which schematically illustrates a method 2000 for brain stimulation by changing electrode selection within an electrode group during stimulation. The method 2000 begins by placing the electrode groups/arrangements on the head of the user (step 2002), then the stimulation signal properties may be determined (step 2004), and electrodes within the electrode groups are selected to form at least one cluster of selected contacts/electrodes forming an emulated electrode (step 2006), and stimulation signal is provided to the user therethrough (step 2008). Then, after a certain amount/duration of time, a change of electrode selection is performed based on the need thereto (step 2010), and then the stimulation session ends (step 2012) after the session time lapses.

Reference is now made to FIGS. 21a-d, which schematically illustrate a multi-group stimulation device 2100 which includes a control circuitry 2102 which is configured to control a signal generator 2104 to provide a stimulation signal through a plurality of electrode array groups, such as first electrode array 2110, second electrode array 2111, third electrode array 2112, fourth electrode array 2113, fifth electrode array 2114, and sixth electrode array 2115.

In some examples, an alteration of electrode selection can be within a certain electrode group.

Figure 21A:
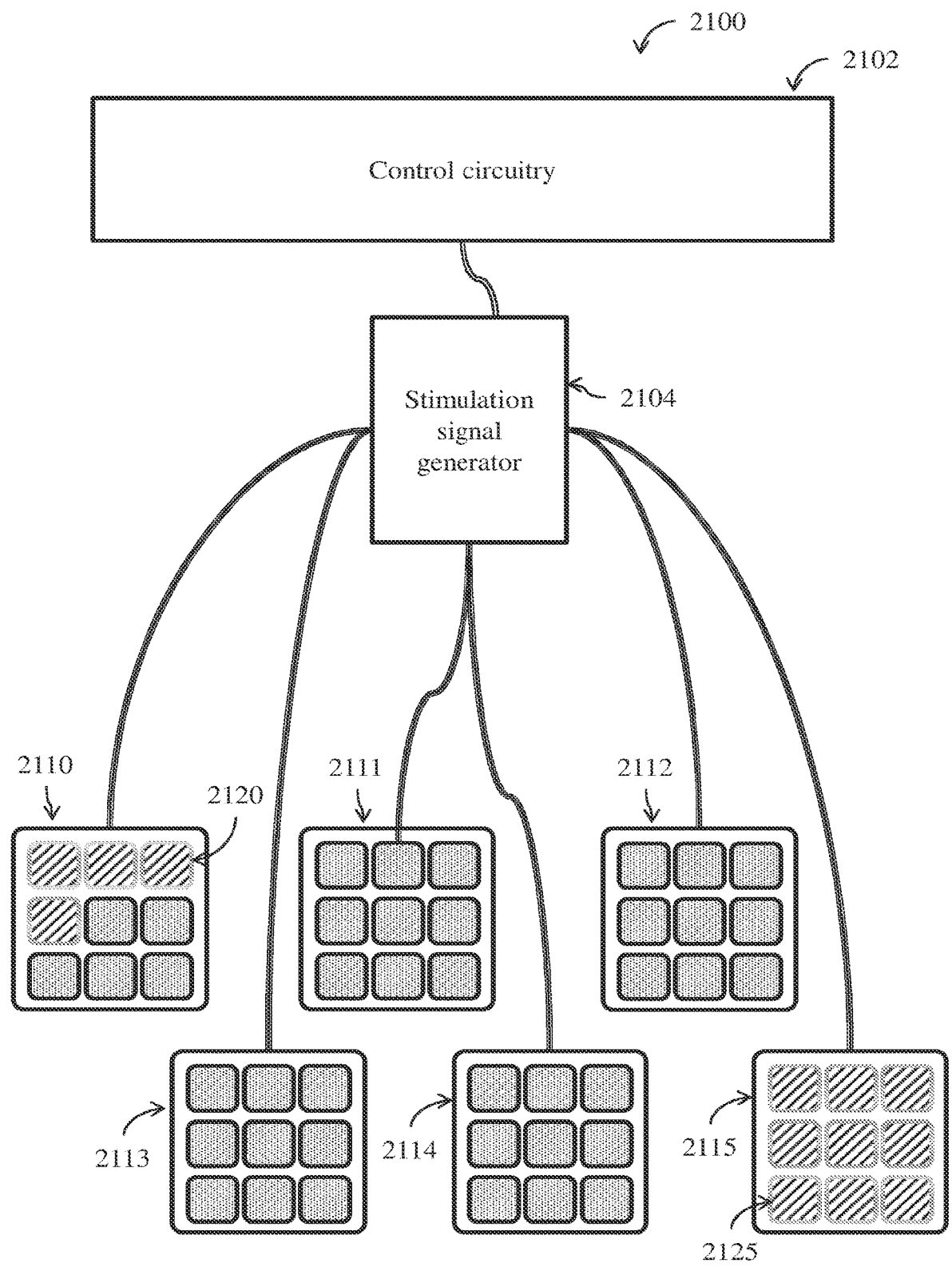
FIGS. 21a-d schematically illustrate a multi-group stimulation device, according to some embodiments.

FIG. 21a illustrates the device 2100, wherein all electrodes 2125 of sixth electrode array 2115 are selected to have a certain polarity or association with signal generator 2104, while a sub-set 2120 of electrodes within first electrode array 2110 are selected to have a different polarity or association with signal generator 2104.

Figure 21B:
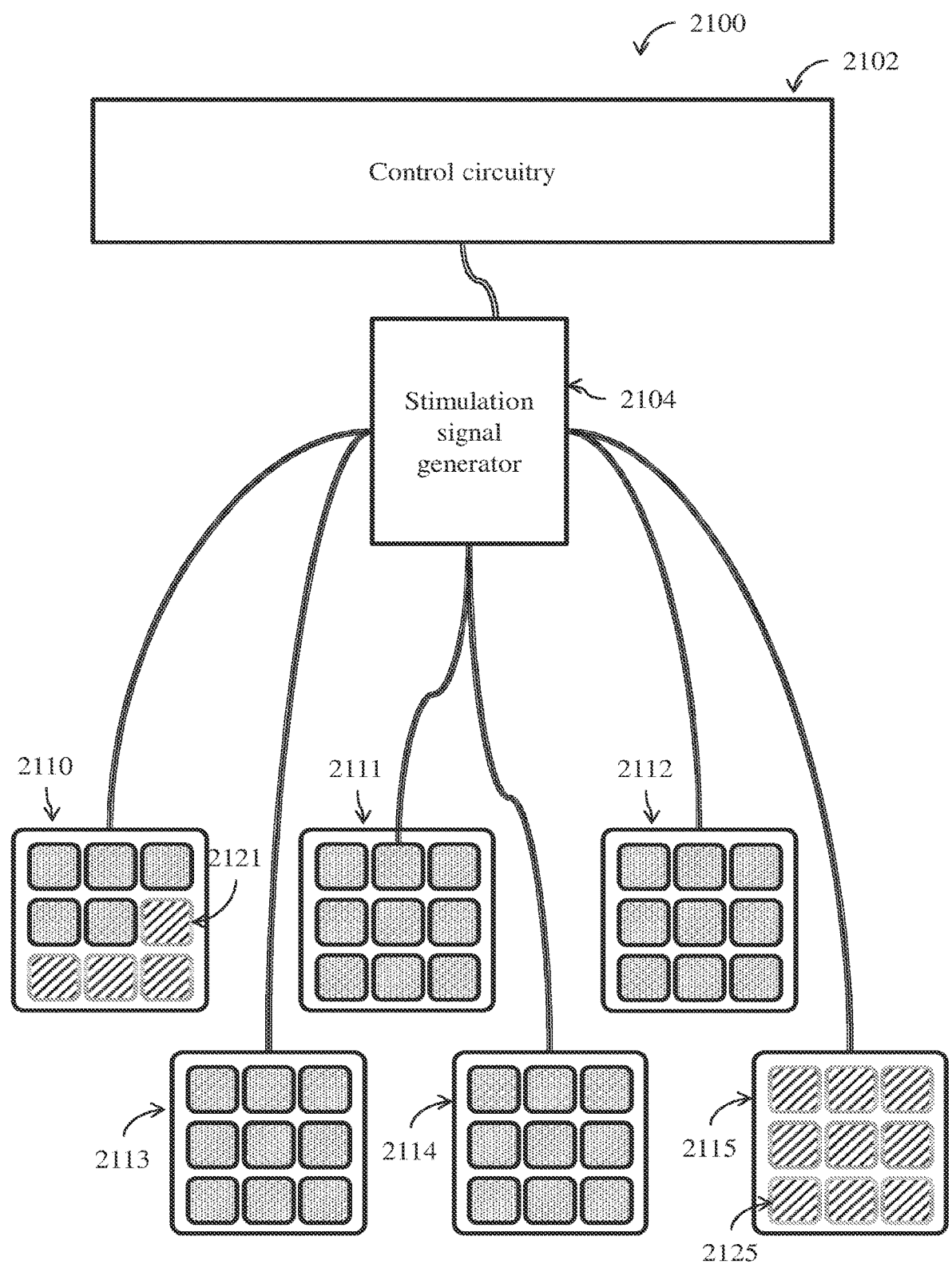

FIG. 21*b* illustrates the device 2100, wherein all electrodes 2125 of sixth electrode array 2115 are selected to have a certain polarity or association with signal generator 2104, as in FIG. 21*a*, while a change in electrode selection occurs within the first electrode array 2110, such that a second sub-set 2121 of electrodes within the first electrode array 2110 are selected to have a different polarity or association with signal generator 2104.

In some examples, an alteration of electrode selection may be between different electrode groups.

Figure 21C:
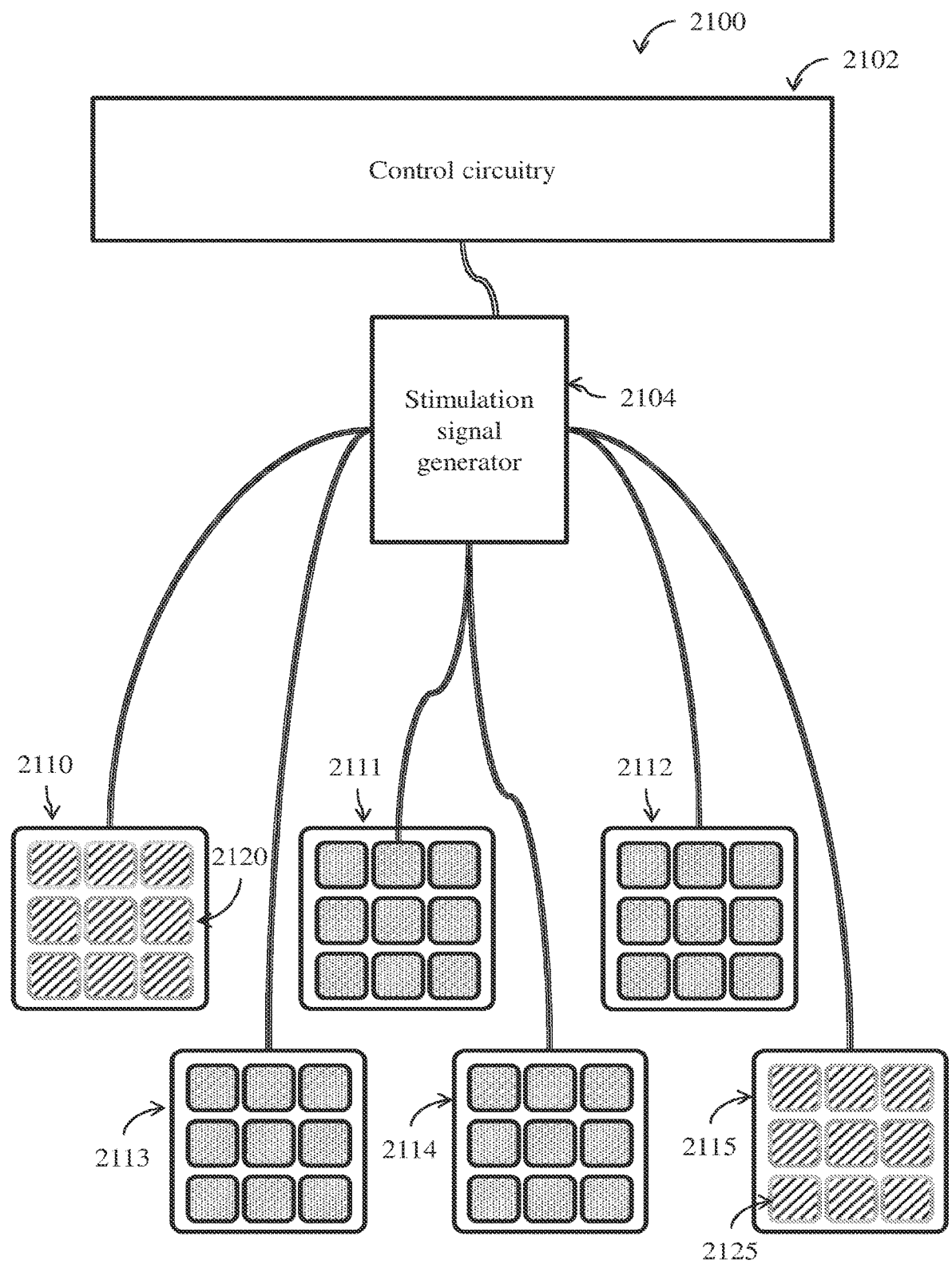

FIG. 21*c* illustrates the device 2100, wherein all electrodes 2125 of sixth electrode array 2115 are selected to have a certain polarity or association with signal generator 2104, and all electrodes 2120 of first electrode array 2110 are selected to have a different polarity or association with signal generator 2104.

Figure 21D:
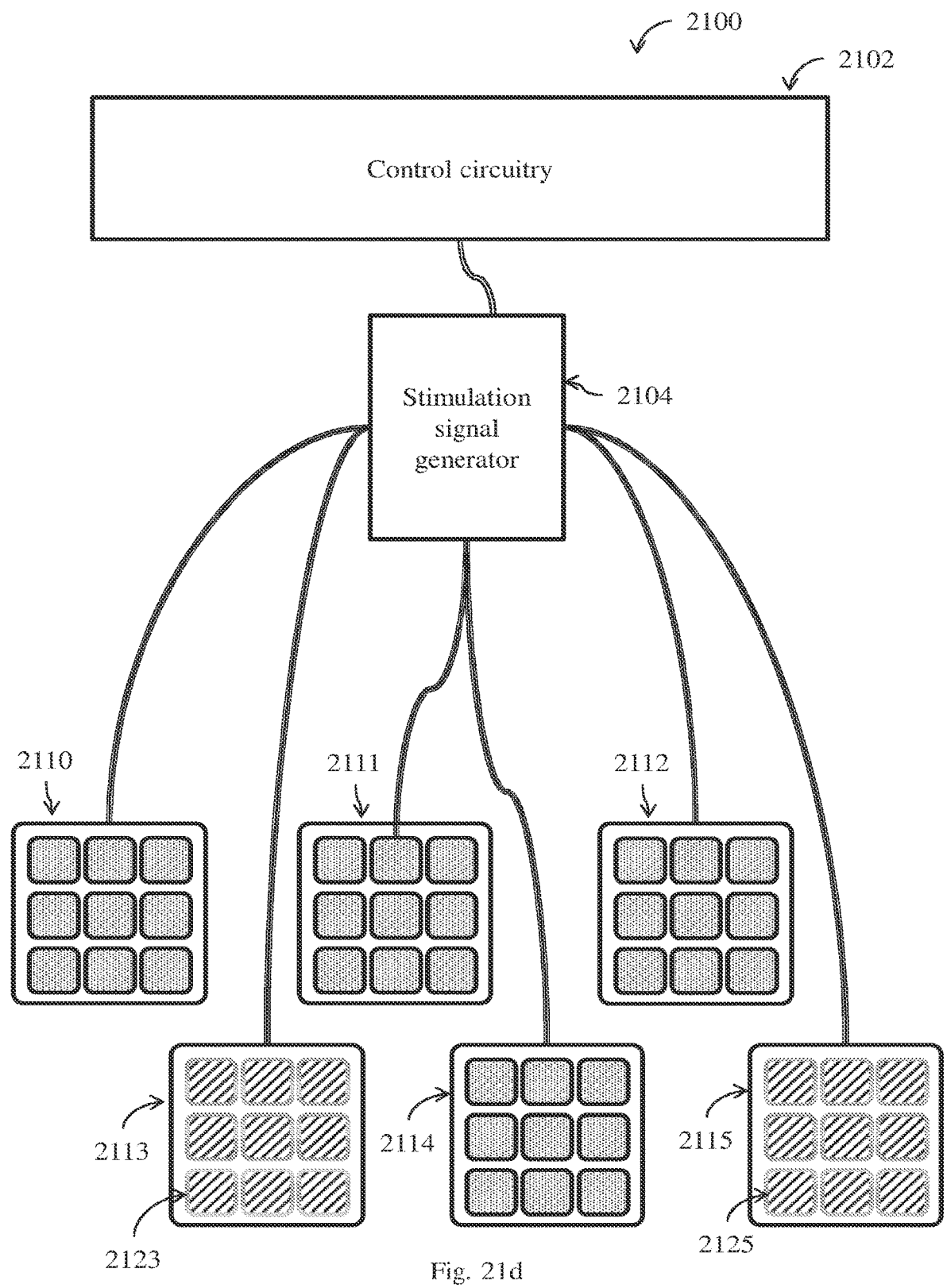

FIG. 21*d* illustrates the device 2100, wherein all electrodes 2125 of sixth electrode array 2115 are selected to have a certain polarity or association with signal generator 2104, as in FIG. 20*c*, while a change in electrode selection occurs between first electrode array 2110 and fourth electrode array 2113, such that all electrodes 2123 of fourth electrode array 2113 are selected to have a different polarity or association with signal generator 2104.

Figure 22:
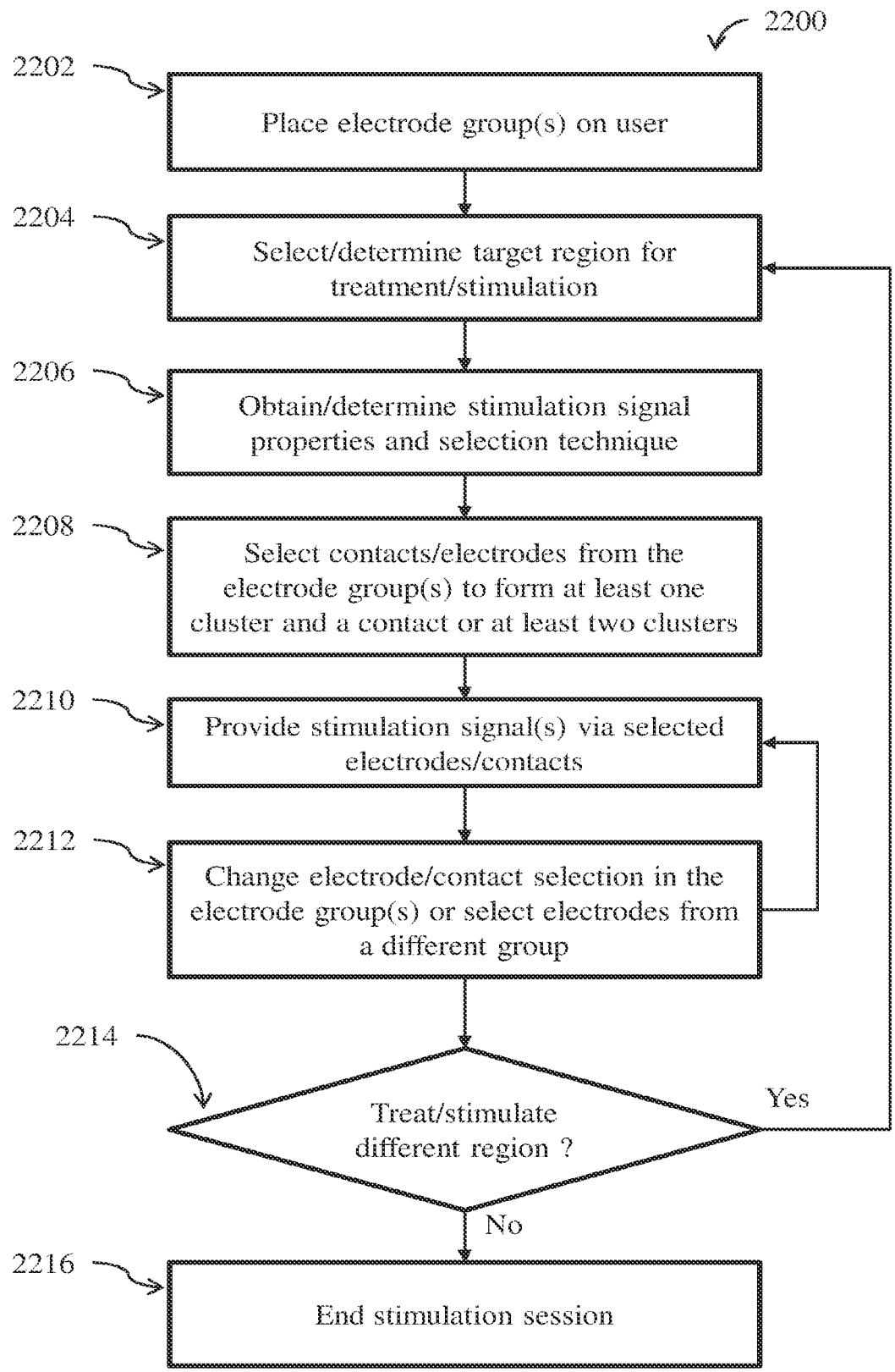
FIG. 22 schematically illustrates a method for multi-region brain stimulation utilizing a multi-group stimulation device, according to some embodiments.

Reference is now made to FIG. 22, which schematically illustrates an example of a flow diagram 2200 of a method for multi-region brain stimulation, which can be used with the system 2100 for example. The method 2200 begins with placing the electrodes or electrode groups on the user or head of the user (step 2202), then a target region is determined for providing stimulation (step 2204), and stimulation signal properties and stimulation technique are determined/obtained (step 2206). Additionally, electrodes within the electrode arrays/groups are selected to provide accurate stimulation to the desired target brain region (step 2208), and stimulation signal is provided via the selected electrodes (step 2210). Optionally, after a certain time period, the electrode selection may be altered for one or more times during the stimulation of the target brain regions to achieve a certain effect, such as cancelling/mitigating the inhibition (step 2212), then, if treatment to further target brain regions is desired (step 2214), a different brain region is selected (step 2204), otherwise the stimulation ends (step 2216).

It should be noted that alternatively to use of the above described electronic selection and re-selection of electrodes to define various desired effective electrodes, a plurality of different electrodes' arrangements can be provided, each designed for stimulation of the desired target in accordance with the target location and geometry. Thus, in this case the stimulation system may include a set of different electrodes' arrangement each with its built-in stimulation unit (signal generator and control circuitry), and the control circuitry is preprogrammed to operate the electrodes' arrangement to provide the desired stimulation field intensity, duration, etc.

As described above, the multiple use of an electrode may deteriorate its functionality and therefore it is desired to provide a technique for identifying the efficiency of electrodes to thereby alert the user and enable exchanging the mal-functioning electrode in good time. There are therefore provided herein electrodes and stimulation systems with identification mechanisms/modules for electrodes, configured to provide the stimulation device with the ability to detect and identify the electrodes that are connected thereto for providing a stimulation signal.

According to some embodiments, the electrodes may have a conductive contact configured for providing a stimulation signal with a limit of the total amount of charge in the lifetime thereof.

According to some embodiments, the stimulation device is configured to save the activity, or a parameter indicative of the activity of the electrode, and determine when the electrode is not recommended for further use.

According to some embodiments, the electrode arrangement includes a plurality of electrodes (sub electrodes), and the process of life-time evaluation and usage history is done per sub electrode. According to some embodiments, the lifetime of an electrode arrangement may be determined by the worst lifetime of its sub electrodes.

According to some embodiments, the systems may be configured to determine whether a certain electrode is able to carry a stimulation session, based on the historic use of the electrode (or sub electrodes thereof) and the stimulation signal characteristics of the current stimulation session.

According to some embodiments, the identification mechanism may include a unique capacitive, resistive, inductive, foot-print. According to some embodiments, the identification may be done using a circuitry with an embedded identification. According to some embodiments, the usage history of an electrode may be stored on a non-transitory memory on the identification module itself.

It is advised, and sometimes required that a stimulation is carried under certain limitation to the stimulation signal. One of the limitation includes "current density", which is the density of the current over area provided to the subject. The current density can be calculated by dividing the amount of current provided to the subject, over the contact area through which the current is provided. Commonly, there is a threshold of current density which should not be surpassed/reached. This threshold may vary depending on the subjects' age, gender, stimulation location, skin sensitivity and more. Therefore, for a current density to be evaluated/determined, the area of the electrode contact with the body of the subject needs to be known.

Thus, there are provided herein electrodes, systems and methods for evaluating stimulation parameters by introducing an electrode with an identification module, and a stimulation system that is configured to derive the electrode properties based on the identification of the electrode. The stimulation system may be configured to evaluate/determine a current density based on the electrode identified using the identification module. When an electrode or electrode structure may include a plurality of sub electrodes, the stimulation system may identify the electrodes characteristics, such as dimensions of each sub electrode, and determine/evaluate the current density based on the identified characteristics, the sub-electrode selection and stimulation signal characteristics.

Figure 23A:
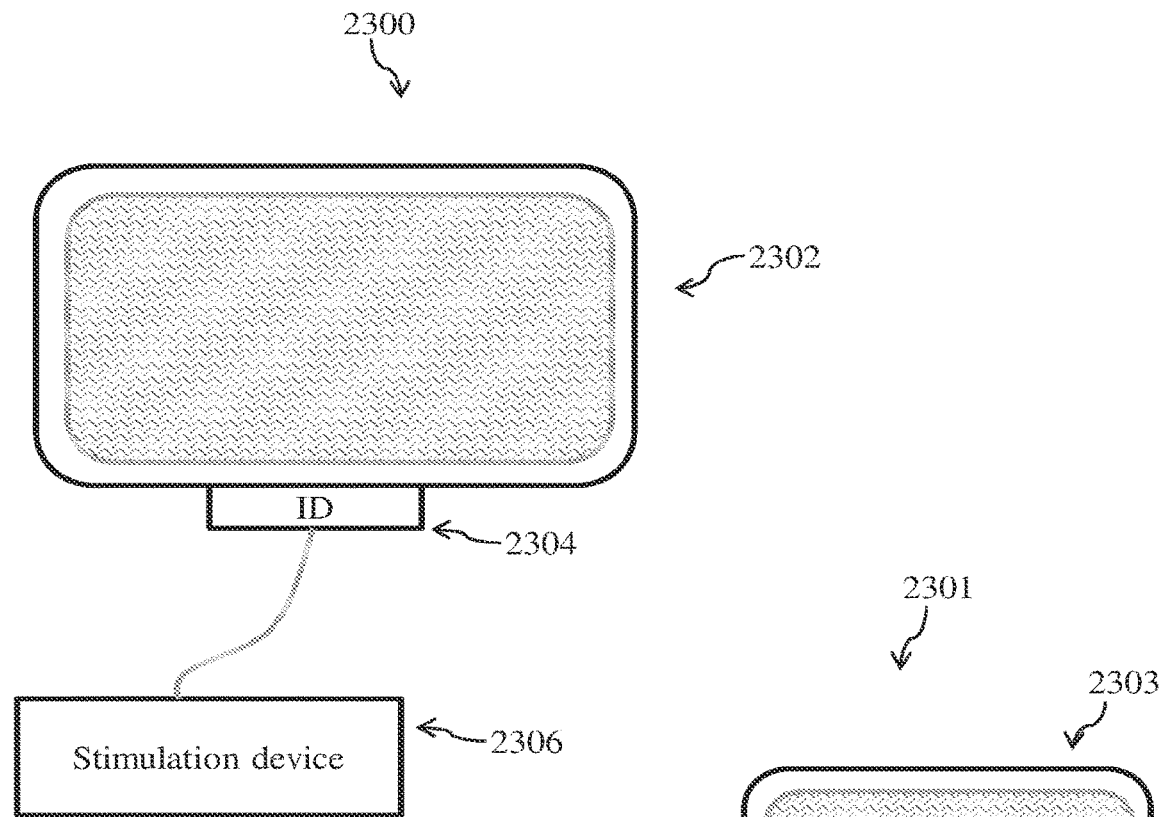
FIG. 23a schematically illustrates a large stimulation electrode with an identification module, according to some embodiments.

Reference is made to FIG. 23*a*, which schematically illustrates a setting 2300 with a large stimulation electrode 2302 and an identification module 2304, connected (configured to be connected) to a stimulation device 2306. The stimulation device 2306 is configured to identify electrode 2302 and derive characteristics, such as dimensions, history of stimulation, expected life time, impedance characteristics, or the like.

According to some embodiments, the stimulation device 2306 is configured to assess whether the identified electrode can be used for delivering a stimulation session based on the characteristics of the electrode, characteristics of the stimulation session, and previous usage of the electrode.

According to some embodiments, the stimulation device is configured to determine stimulation characteristics/parameters based on the characteristics of the stimulation signal, and the characteristics of the electrode.

According to some embodiments, the current density id derived based on the signal intensity and the contact area of the electrode.

Figure 23B:
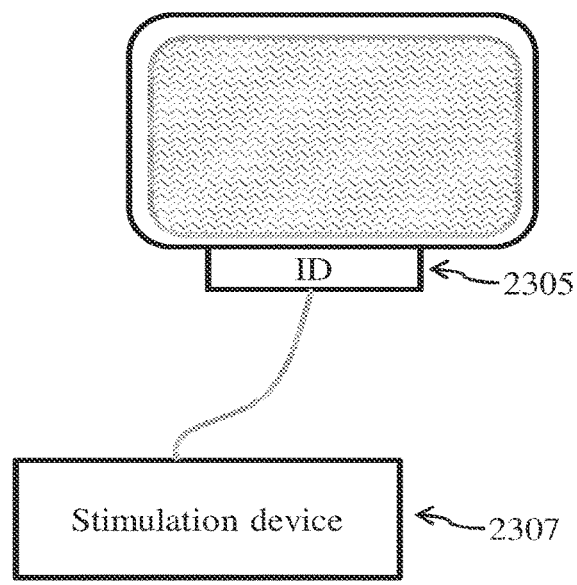
FIG. 23b schematically illustrates a small stimulation electrode with an identification module, according to some embodiments.

Reference is made to FIG. 23b, which schematically illustrates a setting 2301 of a small stimulation electrode 2303 with an identification module 2305 connected to a stimulation device 2307. With electrode 2303 being identified, and detected to be smaller than large electrode 2302, the calculations of the current densities are different, and will show greater densities for the same stimulation signal.

Figure 24:
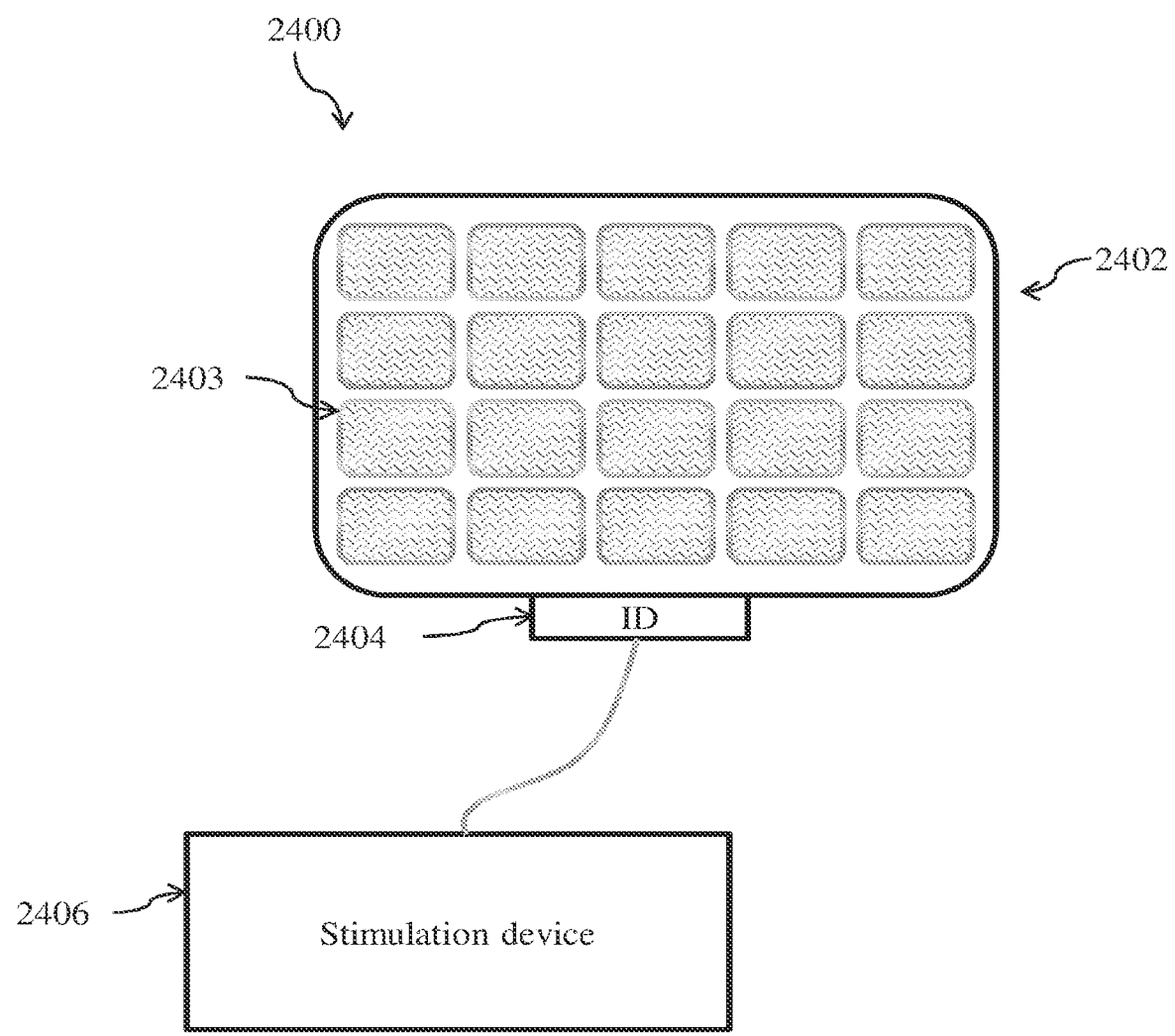
FIG. 24 schematically illustrates an electrode-array with an identification module, according to some embodiments.

Reference is made to FIG. 24, which schematically illustrates a setting 2400 of an electrode-array 2402 including a plurality of sub-electrodes 2403 and an identification module 2404, connected to a stimulation device 2406. The current density may be evaluated based on the characteristics of sub electrodes 2403 as identified by stimulation device 2406, and the selection of sub electrodes, for example by dividing the stimulation current by the sum of the areas of all selected sub-electrodes.

Figure 25:
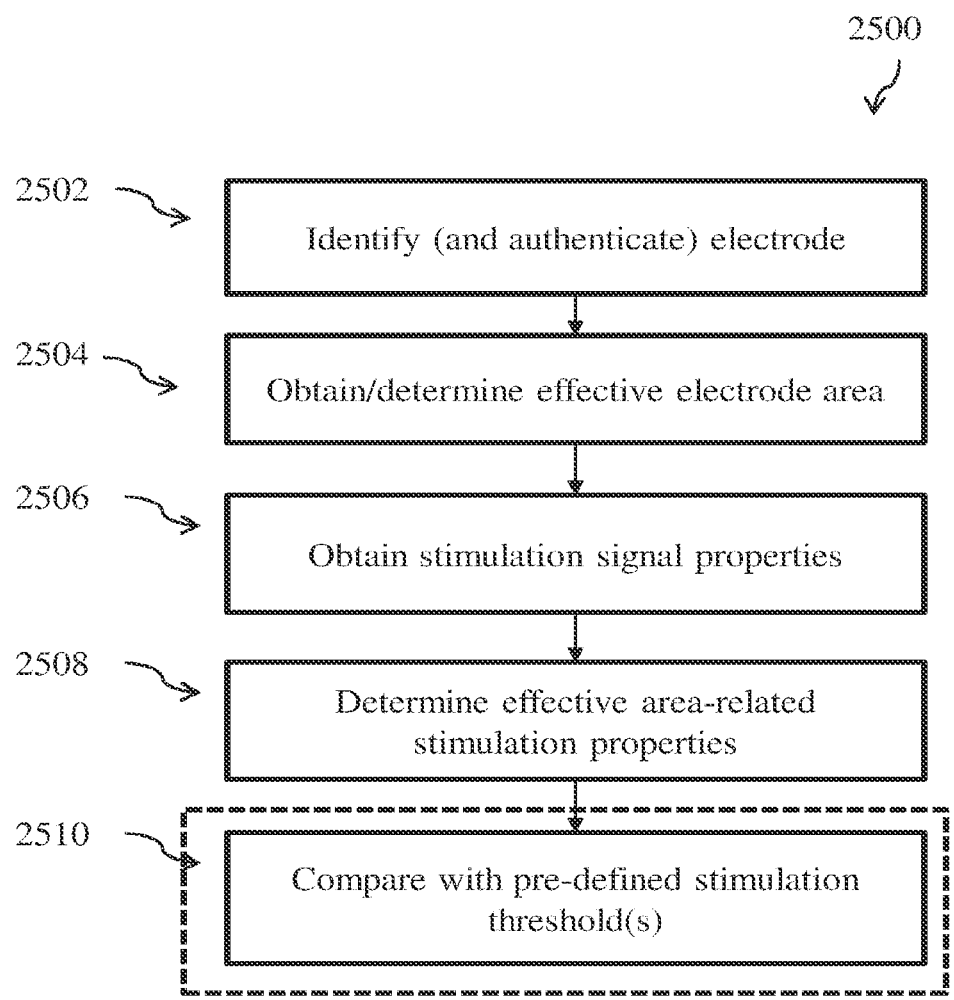
FIG. 25 illustrates a method for electrode identification for meeting stimulation requirements, according to some embodiments.

Reference is made to FIG. 25, which illustrates a method 2500 for electrode identification for meeting stimulation requirements. The method 2500 begins by identifying an electrode connected to the stimulation device (step 2502), then the effective electrode or sub electrodes area is identified (step 2504), and the stimulation signal properties are obtained (step 2506) for determining the effective area-related stimulation parameter. (such as current density) of the electrode contact, such as by adding the areas of selected sub electrodes (step 2508), and then optionally comparing the stimulation parameter to an existing threshold (step 2510).

Figure 26:
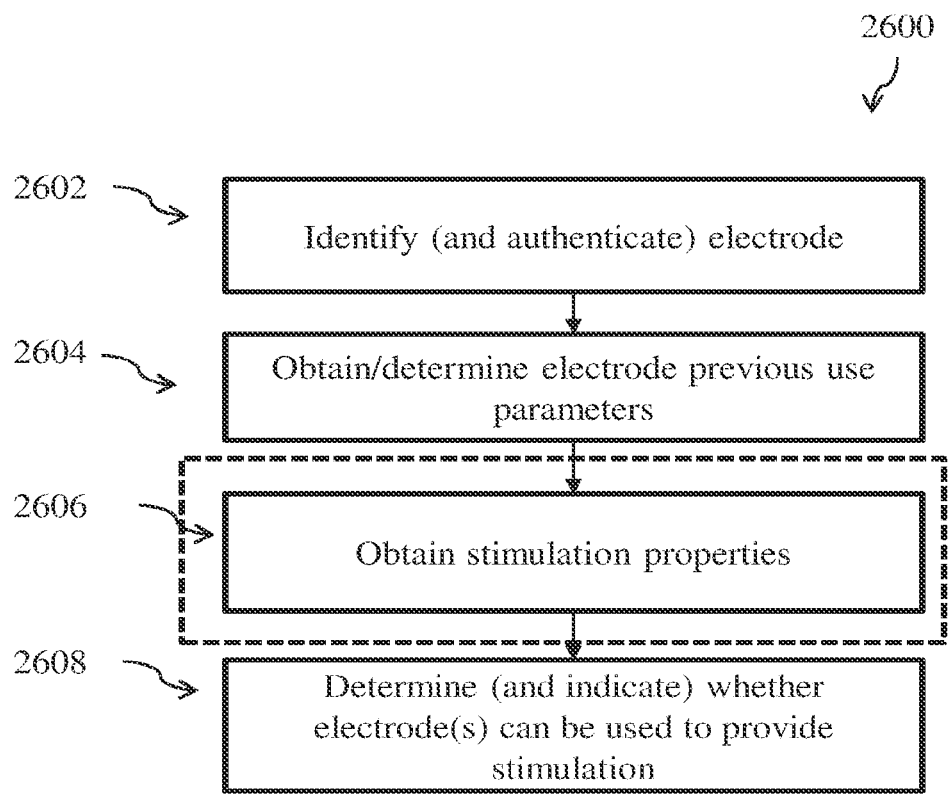
FIG. 26 illustrates a method for electrode identification for life-time calculation of electrodes, according to some embodiments.

Reference is made to FIG. 26, which illustrates a method 2600 for electrode identification for life-time calculation of electrodes. The method 2600 begins by identifying and authenticating a connected electrode (step 2602), then obtaining electrodes historic usage profile (step 2604), optionally, obtaining stimulation session properties (step 2606) and determining, and optionally indicating, whether the identified electrode can be used for providing the stimulation session (step 2608).

As described above, at times the electrodes are spaced from each other with a minimum distance so that the stimulation signal does not pass directly from one electrode to the other neighboring one without affecting the body region. However, this constraint limits the ability to stimulate adjacent target regions. Therefore, there are provided electrodes that enable reducing the minimal distance therebetween, to facilitate higher spatial selection resolution giving the ability to stimulate adjacent target regions.

According to some embodiments, there is provided an electrode, including at least one conducting member (contact), configured to be placed on a target region to provide an electric stimulation signal thereto, and an isolation member, configured to buffer between the conducting member, and a surrounding thereof. Advantageously, the isolation member facilitates electric isolation which enables placing at least two electrodes at close vicinity, without (or with minimizing) direct conductance of a stimulation signal between the two electrodes.

Figure 27:
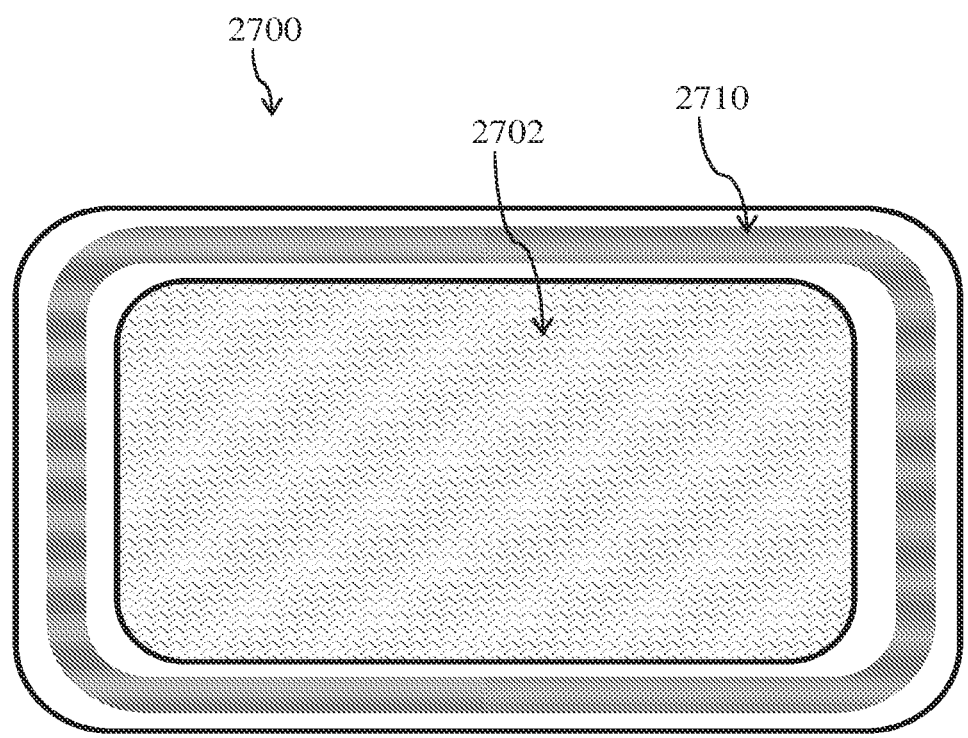
FIG. 27 schematically illustrates an electrode with isolation medium, according to some embodiments.

Reference is made to FIG. 27, which schematically illustrates an electrode 2700 with isolation medium 2710 surrounding a conducting medium 2702. Such a configuration of electrode 2700 facilitates placement of another electrode(s) at close proximity thereto, while minimizing/eliminating the passing of a stimulation signal directly between the electrodes.

According to some embodiments, the isolating member may include synthetic or non-synthetic materials or a combination of both kinds. According to some embodiments, the isolating member may include nylon, such as nylon type 6, type 6.6, type 6.12 or the like. According to some embodiments, the isolating member may include polyester, peek, polyethylene, polypropylene, polystyrene, PTFE, PVC, or the like.

According to some embodiments, the isolating member may have a form or a bulk, a foam, a plurality of threads/bristles, or the like.

According to some embodiments, the isolating member may have a resistance greater than $10^3$ ohm/cm(cm$^2$)(cm$^3$).

According to some embodiments, the isolating member may include rubber, silicone, plastic, thermos-plastics or the like.

According to some embodiments, the isolation member provides the ability to place a plurality of sub electrodes within one structure at a close vicinity. Advantageously, this provides the ability to select between adjacent electrodes to facilitate good spatial selectivity.

Figure 28:
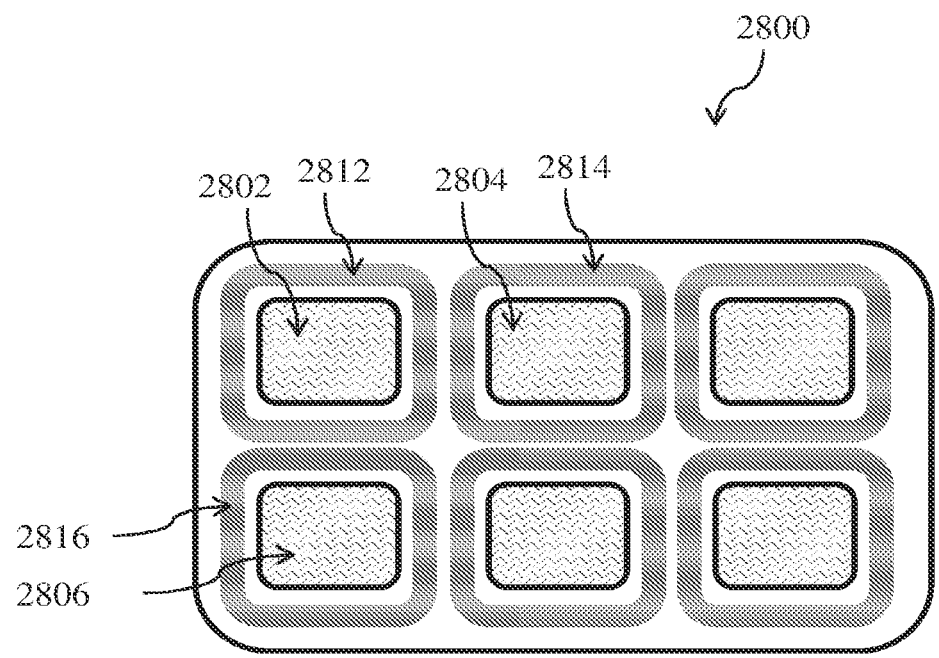
FIG. 28 schematically illustrates an electrode with a plurality of sub electrodes with individual isolation, according to some embodiments.

Reference is made to FIG. 28, which schematically illustrates an electrode 2800 with a plurality of sub electrodes, such as first sub electrode 2802, second sub electrode 2804 and third dub electrode 2806, with individual isolation over sub electrodes, such as first isolation member 2812, second isolation member 2814, and third isolation member 2816, respectively, according to some embodiments.

Figure 29:
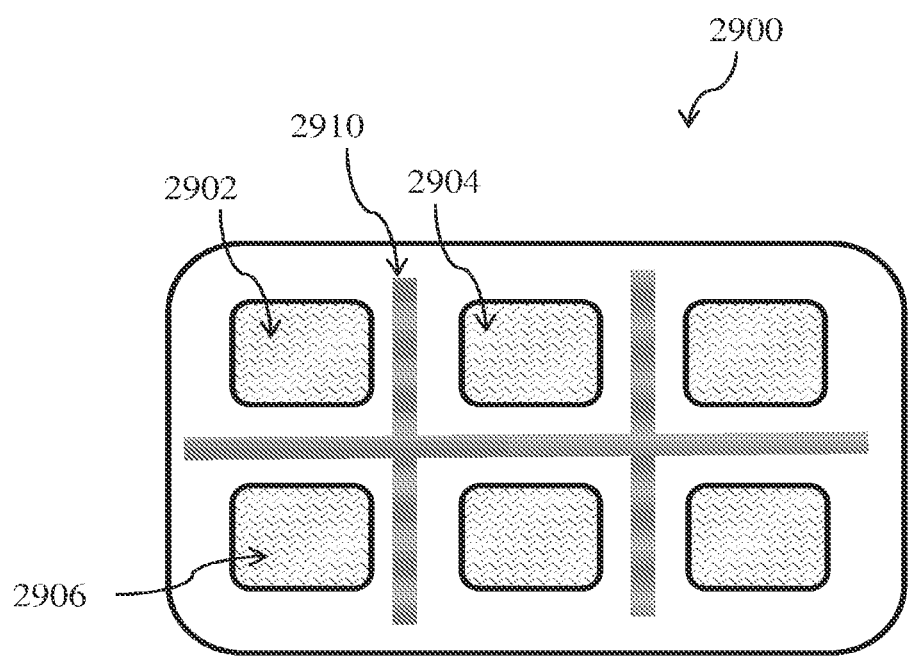
FIG. 29 schematically illustrates an electrode with a plurality of sub electrodes with shared isolation, according to some embodiments, and FIG. 30 schematically illustrates a side view of an electrode with a plurality of conducting members and isolation members, according to some embodiments.

Reference is made to FIG. 29, which schematically illustrates an electrode 2900 with a plurality of sub electrodes, such as first sub electrode 2902, second sub electrode 2904 and third sub electrode 2906, with shared isolation structure 2910 in the form of crossing lines configured to provide electric isolation between different sub electrodes within electrode 2900, especially when placed on the target region of a subject.

Figure 30:
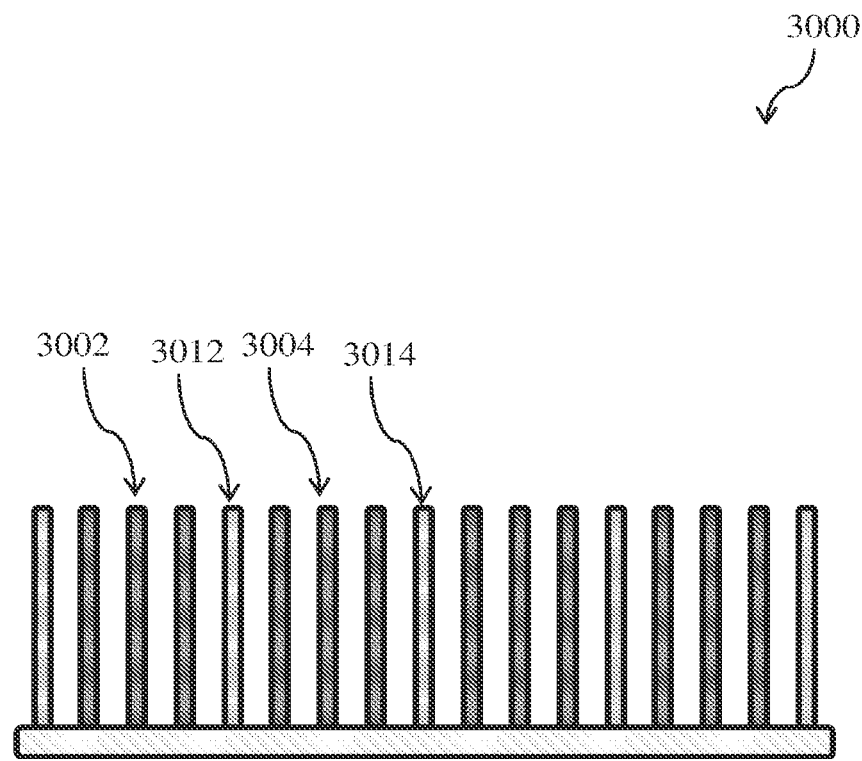

Reference is made to FIG. 30, which schematically illustrates a side view of an electrode 3000 with a plurality of conducting members, such as first conducting member 3002, and second conducting member 3004, with isolation members providing electric separation therebetween, such as first isolation member 3012 and second isolation member 3014.

As mentioned, the invention provides for non-invasive treatment of mental disorders, which can be used as alternatives to drugs, through electric stimulation by utilizing the systems and methods described above. The stimulation treatment includes providing a stimulation signal to a certain brain region by selection of electrodes through-which the stimulation signal is provided. As mentioned, the selection of electrodes is made such that electrodes adjacent to the target brain regions are selected.

The stimulation signal can include direct current stimulation, alternating current stimulation, noise stimulation, random noise stimulation, pulse stimulation or the like or any combination thereof.

The mental disorder can be attention deficit hyperactivity disorder, and the associated target brain regions include the Right-Inferior-Frontal-Gyros and/or the Left-Dorsolateral-Prefrontal-Cortex.

The stimulation can be provided to target brain region(s) in a treatment session continuously in a consecutive manner, or simultaneously, or at different time intervals during the stimulation session. As used herein, the terms "stimulation session" and "treatment session" are interchangeable.

In some scenarios, more than one brain region is stimulated simultaneously. For example by applying random noise stimulation to selected brain regions adjacent to the target brain region(s) at the same time. Or, for example by applying direct current stimulation through electrodes such that anodes are selected to be adjacent to the brain region(s) to which stimulated activity is required, and cathodes are selected to be adjacent to the brain regions to which inhibited activity is required.

The stimulation session may have a duration of at least 5 minutes, or may be in the range of 5 minutes to 60 minutes, or in the range of 5 minutes to 40 minutes, or in the range of 5 minutes to 30 minutes or, in the range of 5 minutes to 20 minutes or, in the range of 10 minutes to 30 minutes.

The stimulation session can be segmented to a plurality of segments, each of the segments being configured for treating certain brain region(s) and/or having varying characteristics.

The stimulation session for ADHD may include providing random noise stimulation through electrodes that are adjacent to the right inferior frontal gyros and the left dorsolateral prefrontal cortex simultaneously. The stimulation session for ADHD may be 20 minutes long or more, and segmented to segments each having a duration of at least 5 minutes, at least one of the segments includes providing random noise stimulation or direct current stimulation or a combination thereof, through electrodes that are adjacent to the right inferior frontal gyros or the left dorsolateral prefrontal cortex simultaneously.

The stimulation session may further include blanc intervals, configured to provide a "relax" period between at least some of the segments in the session.

Any of the devices of the invention, as described above, can be configured to have loaded thereon, or on a non-transitory memory therein, a plurality of stimulation sessions.

The device may further include an efficacy assessment mechanism, such as an EEG, NIRS, behavioral tests, cognitive tests, or the like, for assessing the efficacy of the stimulation session. The efficacy assessment mechanism can be configured to provide measurements of certain parameters prior to a stimulation session and/or after a stimulation session. The parameters may include neural activity estimation, measured for example by EEG.

According to some embodiments, electrode selection may be altered based on feedback from one or more of EEG, NIRS, behavioral tests, cognitive tests or the like, to form a "closed-loop" for increasing the efficacy of the stimulation.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A method for treating a user diagnosed with a cognitive disorder comprising:
    placing a first stimulation electrode on the scalp of the user to target a left dorsolateral prefrontal cortex brain region of the user;
    placing a second stimulation electrode on the scalp of the user to target a right inferior frontal gyrus of the user:
    delivering an electrical stimulation signal between the first stimulation electrode and the second stimulation electrode,
    wherein the electrical stimulation signal is comprised of a plurality of frequencies, wherein the electrical stimulation signal is a random noise stimulation signal, and wherein each of the electrodes comprises a plurality of sub electrodes, and isolation members for electric separation therebetween,
    the method further comprising
    emulating electrodes at specific locations by selecting specific sub electrodes of said plurality of sub electrodes for delivering the stimulation signal,
    keeping a contact area of an aggregate of sub electrodes of the selected sub electrodes within a perimeter of an emulated electrode, and
    wherein the selected sub electrodes define an active area and the isolation members therebetween define a dead area, and wherein the selected sub electrodes are selected such that the active area is greater than the dead area.

* * * * *